(12) United States Patent
Breitweiser et al.

(10) Patent No.: US 12,048,830 B2
(45) Date of Patent: Jul. 30, 2024

(54) DELIVERY OF FLUID FROM A SYRINGE

(71) Applicant: KPR U.S., LLC, Mansfield, MA (US)

(72) Inventors: Kenneth M. Breitweiser, Brighton, IL (US); Kurt Schneider, Webster Groves, MO (US); Robert B. Gaines, Lake Saint Louis, MO (US); Thomas G. Lewis, O'Fallon, IL (US); Emma C. Buckles, Hazelwood, MO (US); Michael C. Dorsey, Edwardsville, IL (US); Christopher A. Knauper, St. Charles, MO (US); Ashanti Bryant, St. Louis, MO (US); Meghan Fox, St. Louis, MO (US); Jessica Watts Miller, St. Louis, MO (US)

(73) Assignee: KPR U.S., LLC, Mansfield, MA (US)

( * ) Notice: Subject to any disclaimer, the term of this patent is extended or adjusted under 35 U.S.C. 154(b) by 719 days.

(21) Appl. No.: 16/686,002

(22) Filed: Nov. 15, 2019

(65) Prior Publication Data

US 2020/0282135 A1   Sep. 10, 2020

Related U.S. Application Data

(60) Provisional application No. 62/814,989, filed on Mar. 7, 2019.

(51) Int. Cl.
*A61M 5/168*   (2006.01)
*A61M 5/14*   (2006.01)
(Continued)

(52) U.S. Cl.
CPC .... *A61M 5/16822* (2013.01); *A61M 5/14232* (2013.01); *A61M 5/14526* (2013.01);
(Continued)

(58) Field of Classification Search
CPC .......... A61M 5/16822; A61M 5/14526; A61M 5/14232; A61M 2240/00; A61M 2202/08;
(Continued)

(56) References Cited

U.S. PATENT DOCUMENTS 7,347,837 B2   3/2008   Azzolini
7,543,516 B2   6/2009   Siefert
(Continued)

FOREIGN PATENT DOCUMENTS

EM   003127083-0006   5/2016
WO   WO 2005/102416 A1   11/2005
(Continued)

OTHER PUBLICATIONS

Narayanan, I., et al., "Fat Loss During Feeding of Human Milk", Queen Charlotte's Maternity Hospital, London, Arch Dis Child: first published as 10.1136/adc.59.5.475, pp. 475-477, May 1, 1984.

*Primary Examiner* — Lauren P Farrar
(74) *Attorney, Agent, or Firm* — ArentFox Schiff LLP

(57) ABSTRACT

An apparatus and method for delivering fluid from a syringe to a subject using a pumping device of a flow control apparatus. The method includes locating the flow control apparatus on a horizontal support surface. Providing the syringe with a volume of fluid including a total amount of preferred nutrient and an amount of non-preferred nutrient liquid. Mounting the syringe relative to the flow control apparatus whereby the syringe is oriented in a generally vertical orientation such that an outlet of the syringe faces upward. Initiating operation of the pumping device to draw the fluid from the syringe for a duration of time to preferentially deliver at least a portion of the total amount of preferred nutrient in the fluid to the subject.

11 Claims, 26 Drawing Sheets

(51) Int. Cl.
*A61M 5/142* (2006.01)
*A61M 5/145* (2006.01)

(52) U.S. Cl.
CPC . *A61M 2005/1403* (2013.01); *A61M 2202/08* (2013.01); *A61M 2205/3306* (2013.01); *A61M 2205/3317* (2013.01); *A61M 2205/3327* (2013.01); *A61M 2205/50* (2013.01); *A61M 2205/52* (2013.01); *A61M 2205/583* (2013.01); *A61M 2205/587* (2013.01); *A61M 2209/084* (2013.01); *A61M 2240/00* (2013.01)

(58) Field of Classification Search
CPC ...... A61M 2209/084; A61M 2205/583; A61M 2205/3306; A61M 2205/3317; A61M 2205/50; A61M 2205/52; A61M 2205/587; A61M 2005/1403; A61M 2205/3327; A61M 2205/502; A61M 2205/12; A61M 5/1456
See application file for complete search history.

(56) References Cited

U.S. PATENT DOCUMENTS

| | | | |
|---|---|---|---|
| 7,758,551 B2 | 7/2010 | Wiesner et al. | |
| 7,879,025 B2 | 2/2011 | Jacobson et al. | |
| 8,161,810 B2 | 4/2012 | Cadieux et al. | |
| 8,574,190 B2 | 11/2013 | Francis | |
| 8,715,215 B2 | 5/2014 | Kopperschmidt | |
| 9,022,981 B2 | 5/2015 | Oesterreich et al. | |
| 9,101,713 B2 | 8/2015 | Cowan et al. | |
| 9,114,207 B2 | 8/2015 | Morris et al. | |
| 9,186,463 B2 | 11/2015 | Hoyle, Jr. | |
| 9,203,227 B2 | 12/2015 | Oesterreich | |
| 9,265,699 B2 | 2/2016 | Hyun | |
| 9,352,083 B2 | 5/2016 | Heitmeiter et al. | |
| 9,486,573 B2 | 11/2016 | Cowan et al. | |
| 9,651,412 B2 | 5/2017 | Swiegot et al. | |
| 9,710,610 B2 | 7/2017 | Flynn et al. | |
| 9,895,487 B2 | 2/2018 | Duncan | |
| 9,909,688 B2 | 3/2018 | Gaines et al. | |
| 9,974,902 B2 | 5/2018 | Holderle et al. | |
| 9,976,551 B2 | 5/2018 | Blomquist | |
| 10,092,690 B2 | 10/2018 | Gillespie et al. | |
| 10,238,790 B2 | 3/2019 | Toro et al. | |
| 10,240,959 B2 | 3/2019 | Eckel et al. | |
| 10,292,908 B2 | 5/2019 | Hyun et al. | |
| 10,500,340 B2 | 12/2019 | Rios et al. | |
| 10,543,312 B2 | 1/2020 | Cowan | |
| 10,682,286 B2 | 6/2020 | Nordquist et al. | |
| 10,694,986 B2 | 6/2020 | Hoan et al. | |
| 10,709,835 B2 | 7/2020 | Clarke | |
| 10,874,793 B2 | 12/2020 | Oruklu et al. | |
| 10,926,043 B2 | 2/2021 | Cowan et al. | |
| 10,971,260 B2 | 4/2021 | Searle et al. | |
| 11,020,322 B2 | 6/2021 | Elia et al. | |
| 11,020,541 B2 | 6/2021 | Fangrow et al. | |
| 11,045,396 B2 | 6/2021 | First et al. | |
| 11,077,027 B2 | 8/2021 | Pineda et al. | |
| 11,147,917 B2 | 10/2021 | Wolff | |
| 11,160,731 B2 | 11/2021 | Wiesner | |
| 11,185,474 B2 | 11/2021 | Elia et al. | |
| 11,217,340 B2 | 1/2022 | Desch et al. | |
| 11,259,992 B2 | 3/2022 | Harr | |
| 2011/0315611 A1* | 12/2011 | Fulkerson | A61M 1/1696 210/96.2 |
| 2014/0031784 A1 | 1/2014 | Flynn et al. | |
| 2014/0046296 A1* | 2/2014 | Clarke | G16H 20/17 604/507 |
| 2014/0242213 A1 | 8/2014 | Mccarty et al. | |
| 2016/0256621 A1* | 9/2016 | Toro | A61M 5/008 |
| 2016/0263310 A1 | 9/2016 | Helbig | |
| 2017/0333623 A1* | 11/2017 | Kamen | A61M 5/1413 |
| 2018/0028761 A1* | 2/2018 | Anand | A61M 5/2033 |
| 2019/0381252 A1* | 12/2019 | Joseph | A61M 5/3129 |
| 2020/0163843 A1 | 5/2020 | Francis | |
| 2020/0171241 A1 | 6/2020 | Kamen et al. | |
| 2020/0197942 A1 | 6/2020 | Wegener et al. | |
| 2020/0289751 A1 | 9/2020 | Despa et al. | |
| 2021/0128801 A1 | 5/2021 | Poppe et al. | |

FOREIGN PATENT DOCUMENTS

| | | |
|---|---|---|
| WO | WO 2015/048743 A2 | 4/2015 |
| WO | WO 2018/022355 A1 | 2/2018 |

* cited by examiner

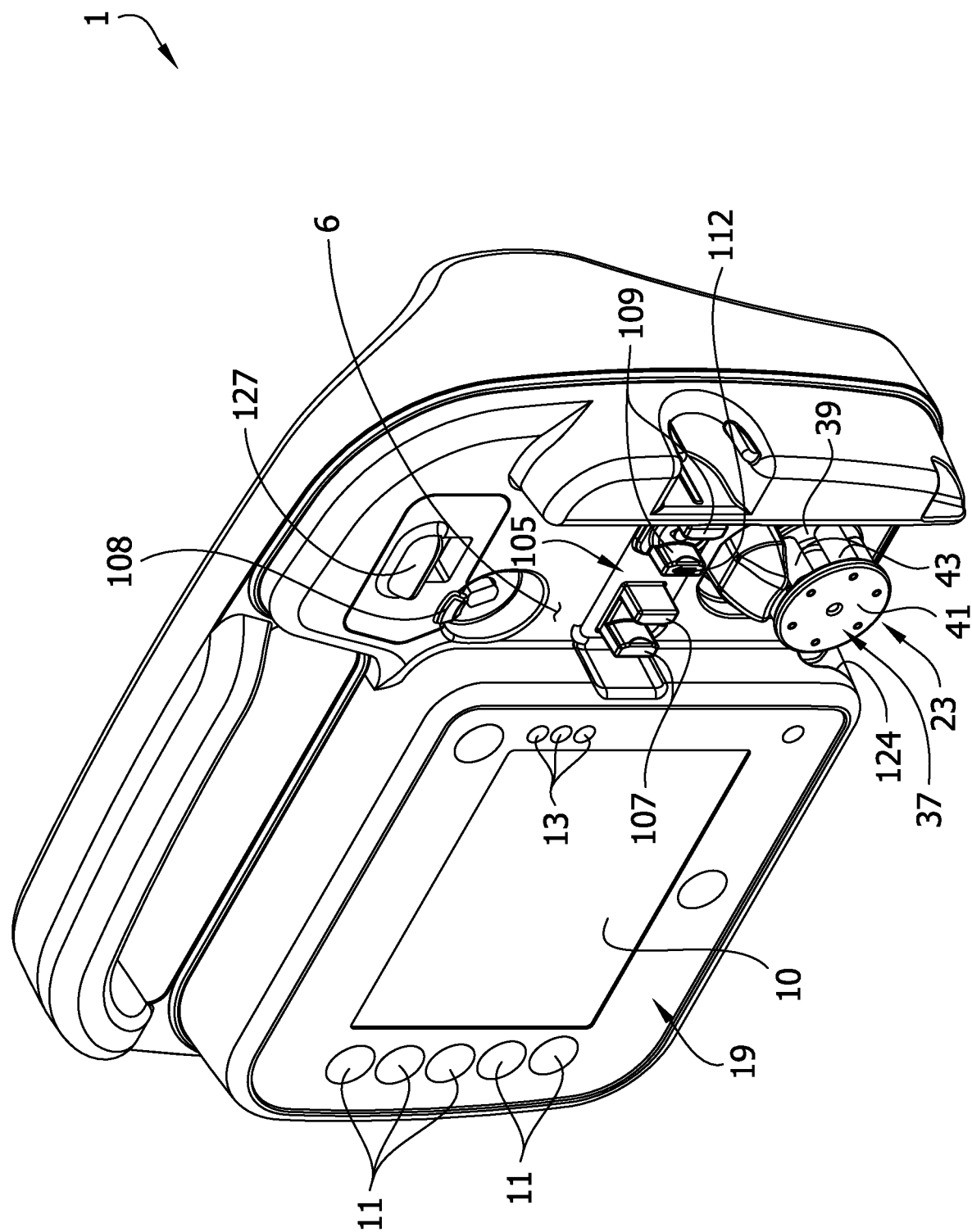

DELIVERY OF FLUID FROM A SYRINGE

CROSS-REFERENCE TO RELATED APPLICATION

This application claims priority to U.S. Provisional Patent Application Ser. No. 62/814,989, filed Mar. 7, 2019, which is hereby incorporated by reference in its entirety.

FIELD

The present invention generally relates to delivery of fluid from a syringe, and more particularly to a pump set, syringe stand, syringe assembly, flow control apparatus and associated methods to deliver fluid from the syringe.

SUMMARY

Administering medicine or nutrition to a patient who cannot intake the medicine or nutrition orally can be effected by utilizing peristaltic flow control systems. Typically in such systems, fluid is delivered to the patient by a pump set including a flexible elastomeric tubing loaded on a flow control apparatus, such as a peristaltic pump, which delivers fluid to the patient at a controlled rate of delivery. The peristaltic pump usually has a housing that includes a rotor operatively engaged to a motor through a gearbox. The rotor drives fluid through the flexible tubing of the pump set by the peristaltic action effected by reversible compression created by impingement, e.g., pinching, by one or more rollers on the rotor. Rotation of the rotor progressively compresses the elastomeric tubing that drives the fluid at a controlled rate. The pump set may have a valve mechanism for permitting or preventing fluid flow communication through the pump set. The flow control system may also have a controller that operatively regulates the one or more motors which effectively controls fluid flow.

Peristaltic pumps operate by delivering fluid in small charges called "aliquots". The rotor engages elastomeric tubing of the pump set, pinching off a portion of the elastomeric tubing and pushing fluid forward of the pinch point, e.g., closer to the patient than to the source of fluid toward the patient. Typically, the volume of fluid to be administered to the patient is controlled in the pump by counting the number of aliquots, each being of substantially the same volume, and stopping when the number reaches an amount corresponding to the total desired volume of fluid to be delivered. Peristaltic pumps are sanitary and generally accurate and therefore very useful in the administration of medication and therapeutic fluids to the patient.

In one aspect, a method of delivering fluid from a syringe to a subject using a pumping device of a flow control apparatus generally comprises locating the flow control apparatus on a horizontal support surface. Providing the syringe with a volume of fluid including a total amount of preferred nutrient and an amount of non-preferred nutrient liquid. Mounting the syringe relative to the flow control apparatus whereby the syringe is oriented in a generally vertical orientation such that an outlet of the syringe faces upward. Initiating operation of the pumping device to draw the fluid from the syringe for a duration of time. Delivering at least a portion of the volume of fluid from the syringe to the subject such that at least 40% of the total amount of preferred nutrient in the fluid is delivered from the syringe within a first third of the duration of time the pumping device is operated to draw the fluid from the syringe.

In another aspect, a syringe stand for supporting a syringe including a barrel having an outlet and a plunger received in an end of the barrel opposite the outlet generally comprises a base for supporting the syringe stand on a horizontal support surface. A holder secures the syringe to the syringe stand. The holder is attachable to the base and selectively positionable relative to the base to orient the syringe in at least two different positions.

In yet another aspect, a flow control apparatus for use with a pump set to deliver fluid from a feeding source through the pump set to a subject generally comprises a pumping device capable of acting on the pump set to produce a fluid flow within the pump set during a feeding cycle. A controller is in communication with the pumping device for controlling operation of the pumping device in a feeding configuration for producing flow of a fluid in the pump set. The controller includes a processor and a memory. The controller is adapted to store in the memory a selected flow rate and a desired fluid volume of the fluid. The controller is configured to execute in the processor a feed time compensator to adjust a feed time for operating the pumping device for delivering the fluid through the pump set during the feeding cycle to account for a detected deviation in actual flow rate from the feeding source from the selected flow rate.

In still another aspect, a support for a flow control apparatus including a pumping system for engaging a pump set mounted on the apparatus generally comprises a base for receiving at least a portion of the flow control apparatus. The base is configured to support the flow control apparatus on a horizontal support surface whereby the flow control apparatus is oriented in a generally horizontal orientation. At least one adjustable leg on the base is configured to change an angular orientation of the base with respect to a horizontal axis when the base is supported on the horizontal support surface thereby changing an angular orientation of the flow control apparatus when the flow control apparatus is received in the base.

BRIEF DESCRIPTION OF THE DRAWINGS

FIG. 4 is a front perspective view of the enteral feeding pump;

Corresponding reference characters indicate corresponding parts throughout the drawings.

DETAILED DESCRIPTION

Figure 1:
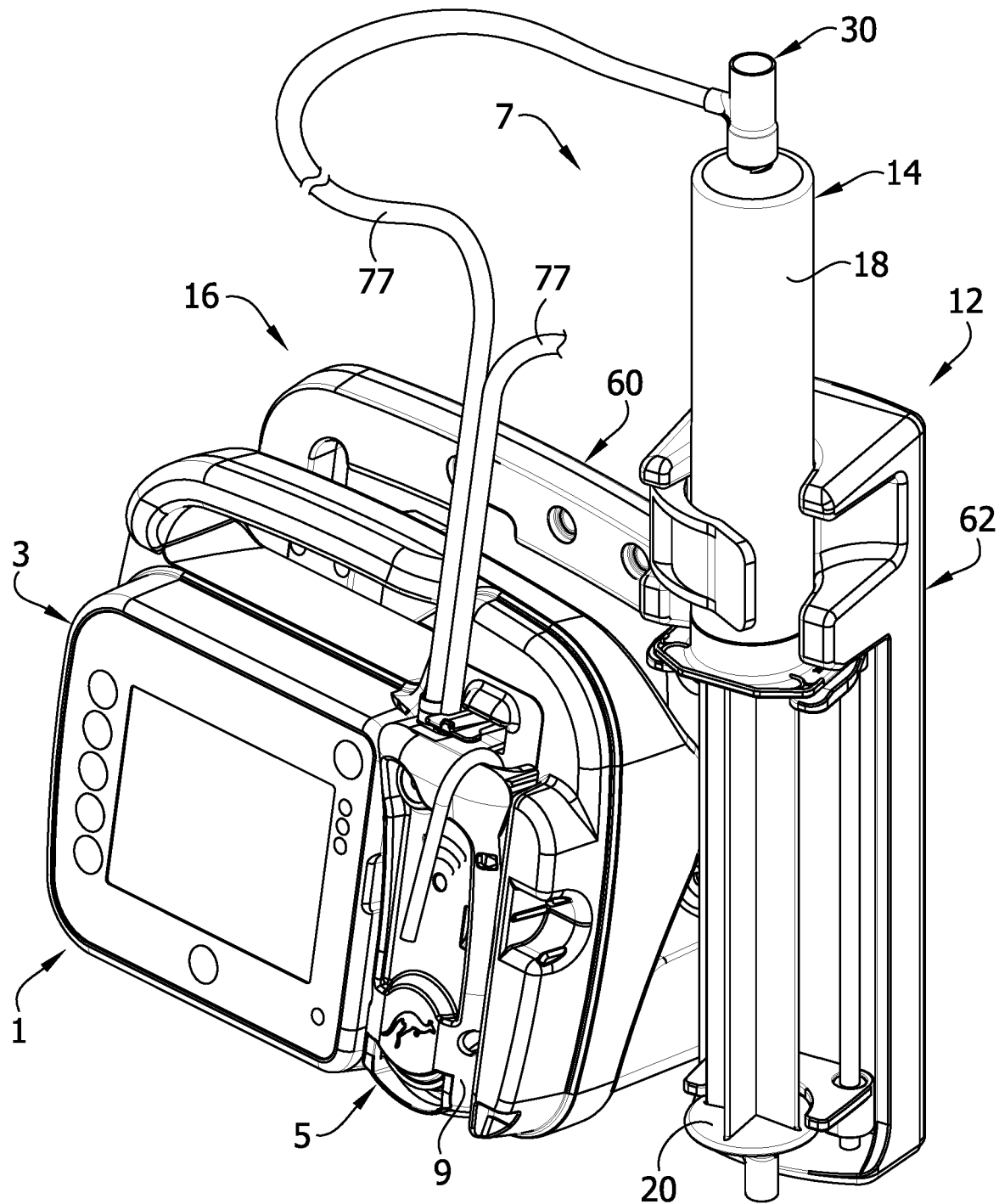
FIG. 1 is a perspective view of a feeding system including an enteral feeding pump, a pump support, a feeding set assembly and a syringe.

One or more aspects of the present invention pertain to peristaltic pumps such as rotary peristaltic pumps and particularly to a feeding set assembly mountable on a rotary peristaltic pump for providing a fluid delivery apparatus that accurately detects and controls the amount of fluid delivered to a patient (e.g., infant) and maximizes nutrient delivery to the patient. Any one or more advantageous features or structures that provide or facilitate any one or more of such features may be implemented in a peristaltic pump employed in various commercial and industrial applications. Thus, although the detailed discussion is directed to an enteral feeding pump with a and feeding set assembly including a cassette, any one or more features of the invention may be embodied or implemented in other peristaltic pumps. For example, although the exemplarily discussed pump is a rotary peristaltic enteral feeding pump, the present invention has application to other types of peristaltic pumps (not shown), including medical infusion pumps. Additionally, one or more of the various features and aspects of the invention may be implemented in peristaltic pumps that use mechanisms other than rollers without departing from the scope of the present invention such as linear peristaltic pumps. Moreover, feeding set assemblies (not shown) that do not include cassettes may also be used within the scope of the present invention.

Referring now to the drawings, and in particular FIGS. 1-6, an exemplary enteral feeding pump (broadly, "flow control apparatus") constructed according to any one or more of the principles of the present invention is generally indicated at 1. The feeding pump may comprise a housing generally indicated at 3 that is constructed so as to mount a cassette, generally indicated at 5, of a feeding set assembly (broadly, a "pump set"), generally indicated at 7. The feeding set assembly 7 may include a syringe assembly 12 connected to the cassette 5 via tubing 77. The cassette 5 of the feeding set assembly 7 is releasably attachable to the housing 3. In the illustrated embodiment, a cassette shell 9 of the cassette is removably received in a cassette recess 6 (FIG. 4) in the housing 3. It will be appreciated that "housing" as used herein may include many forms of supporting structures (not shown), including without limitation multi-part structures and structures that do not enclose or house the working components of the pump 1. The pump 1 may also have a display screen 10 on the housing 3 capable of displaying information about the status and operation of the pump. Moreover, various aspects and features of the present invention can be implemented without the recess 6. One or more buttons 11 which can be proximate the display screen 10 can be provided for use in controlling and obtaining information from the pump 1, and one or more light emitting diodes 13 can provide status information for the pump.

Figure 19:
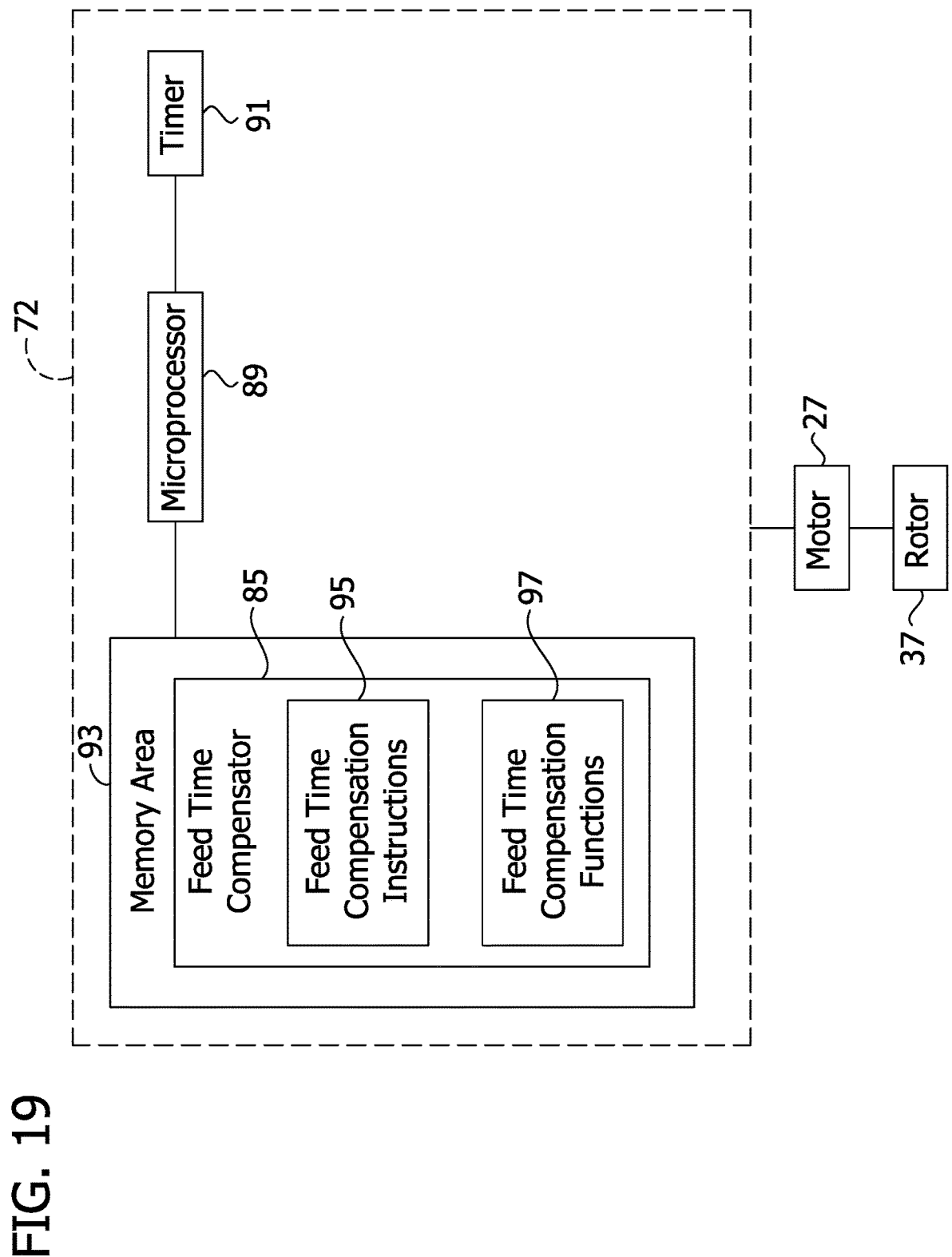
FIG. 19 is a block diagram showing components of the enteral feeding pump that may be utilize to implement one or more aspects disclosed herein.

The display screen 10 may be part of a front panel (generally indicated at 19) of the housing 3 and may be removably attached to the housing. The enteral feeding pump may further include a pumping unit indicated generally at 23 (FIGS. 3 and 4) comprising a pump motor 27 (FIG. 19) connected to a rotor shaft (not shown). A battery (not shown) may be received in the housing 3 for powering the pump motor. A power source other than or in addition to the battery could be used to energize the pump including one or more prime motors which drive the pumping unit through the rotor shaft.

The pumping unit 23 has a rotor (generally indicated at 37) which can be coupled to the rotor shaft. The rotor 37 may include an inner disk 39, an outer disk 41, and four rollers 43 (only three of which are shown) mounted between the inner and outer disks for rotation relative to the disks about their longitudinal axes. The rollers 43 engage a tube 45 (FIG. 3) of the feeding set assembly 7 that forms part of the cassette 5 to deliver fluid through the feeding set assembly 7 to a subject when the cassette 5 is attached to the housing 3. For example nutritional liquid (e.g., breast milk and/or fortifier) may be delivered to an infant using the pump 1, cassette 5, and feeding set assembly 7. Other fluids may also be delivered using the pump 1 without departing from the scope of the disclosure. In the illustrated embodiments, the fluid in the syringe 14 is drawn from the syringe by a vacuum pressure applied by the pumping unit 23. However, certain aspects of the present invention have equal application if the fluid from the syringe 14 is delivered from the syringe in other ways, such as by driving the plunger into the barrel of the syringe.

Figure 5:
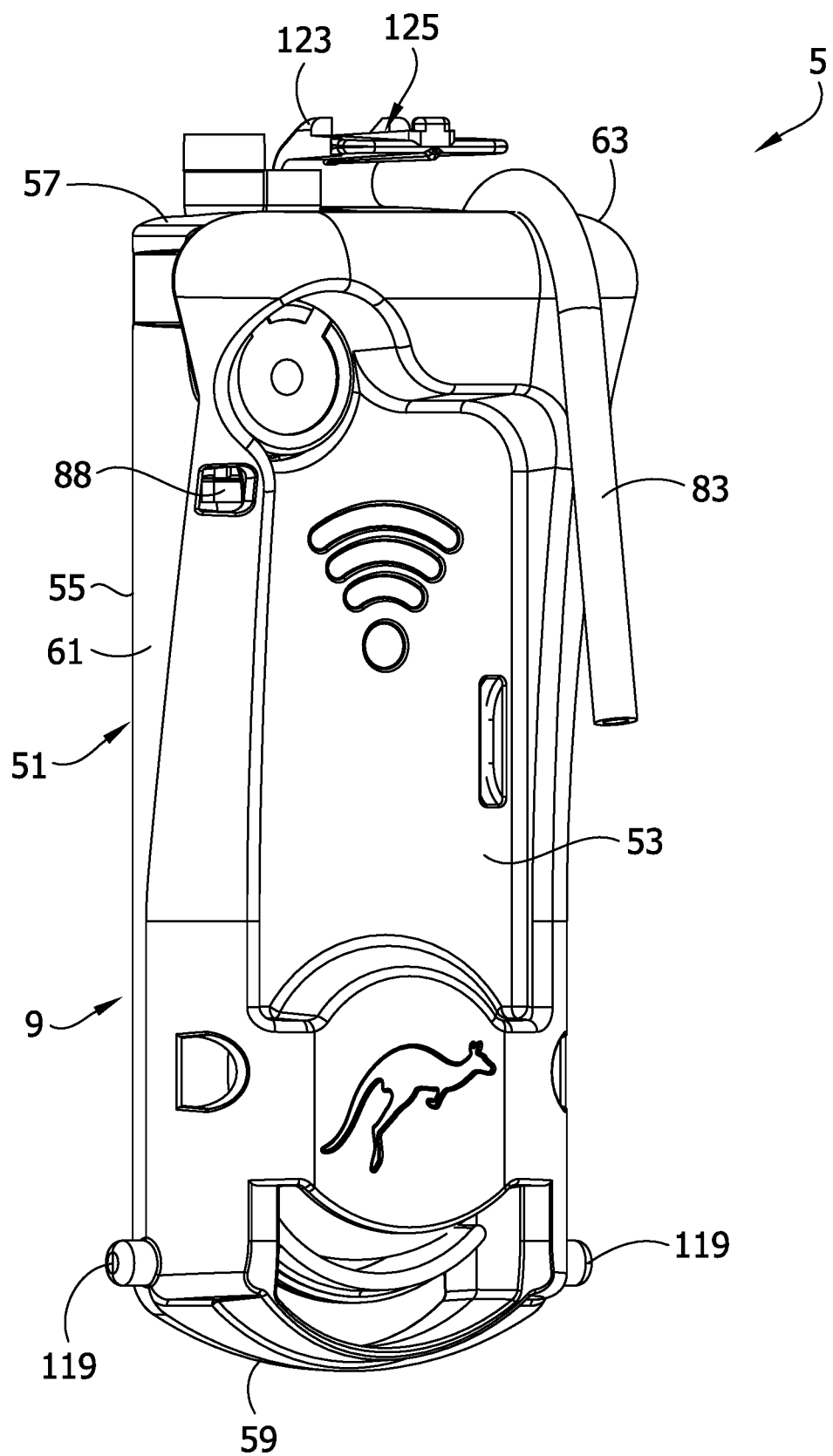
FIG. 5 is a perspective of the cassette.
Figure 6:
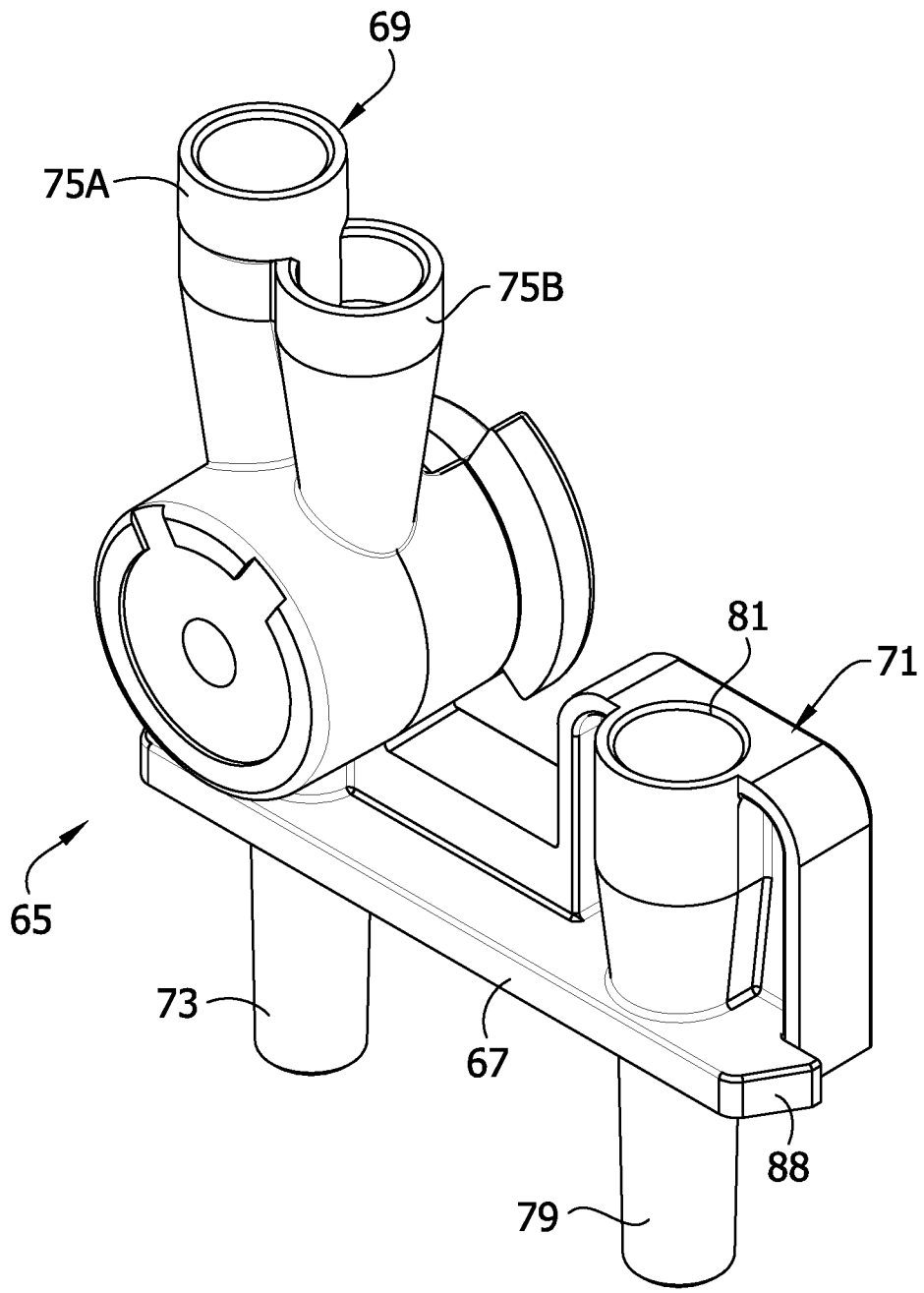
FIG. 6 is a perspective of a fitting of the cassette.

Referring to FIGS. 5 and 6, the cassette shell 9 comprises a cassette body 51 having a front 53, a back 55, a top 57, and a bottom 59. Side walls 61 and top wall 63 may extend from the back 55 of the cassette body 51 forming a back cavity configured for receiving a fitting 65. The tube 45 may be releasably attached to the fitting 65. The fitting 65 may have tabs 88 that allow the fitting 65 to be secured or snapped into the cassette. In some cases, the fitting can be removably secured to the cassette.

Figure 3:
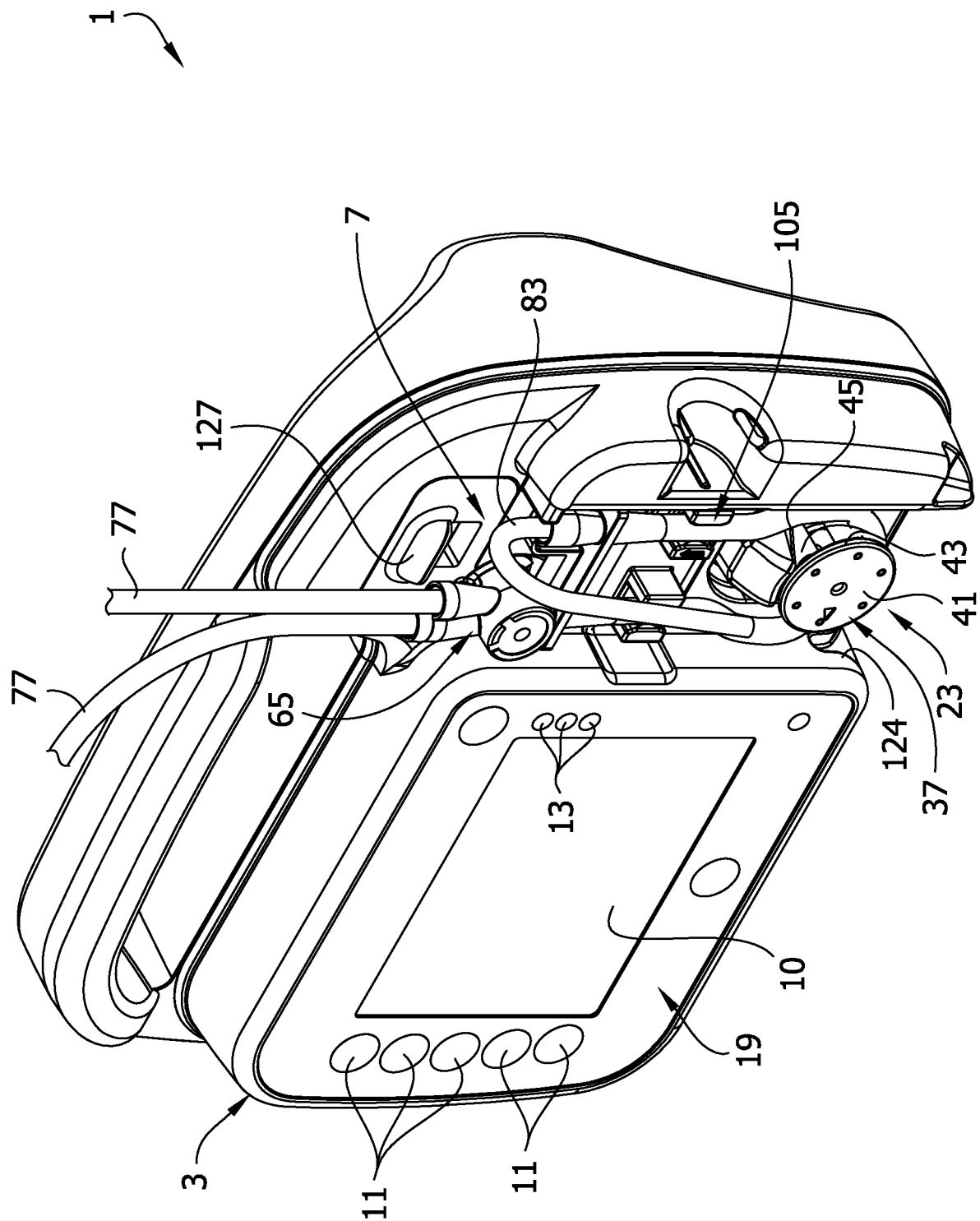
FIG. 3 is the perspective view of FIG. 2, but with portions of the cassette removed.

Referring to FIG. 6, the fitting 65 comprises a base 67, an inlet port 69, and an outlet port 71. The inlet port 69 may include a first attachment portion 73 for insertion into an inlet end of the tube 45, and a pair of second attachment portions 75A, 75B for receiving inlet tubing 77 (FIG. 3). The outlet port 71 may include a first attachment portion 79 for engagement or attachment to, such as by insertion into an outlet end of the tube 45, and a second attachment portion 81 for attachment to such as by receiving outlet tubing 83. Second attachment portion 75A may be placed in fluid communication with a feeding source (e.g., syringe 14), and second attachment portion 75B may be placed in fluid communication with a flushing source (e.g., flushing fluid bag) via the inlet tubing 77. Alternatively, second attachment portion 75B could be attached to the feeding source and second attachment portion 75A could be attached to the flushing source. Alternatively, the fitting 65 may be formed integrally with the cassette body 51, or omitted. Additionally, second attachment 75B could be open to air so that once the feeding of nutritional liquid (e.g., breast milk) through second attachment portion 75A is complete, second attachment portion 75B could be used to clear the line of breast milk by pulling air through the line. This prevents breast milk form being left in the tubing and wasted. It will be understood that second attachment portions 75A and 75B could be switched whereby breast milk is fed through second attachment portion 75B, and the flushing action is performed through second attachment portion 75A without departing from the scope of the disclosure.

The inlet tubing 77, tube 45, fitting 65, and outlet tubing 83 are considered part of the feeding set assembly 7. The cassette 5 is considered to be part of the feeding set assembly 7 for purposes of this description. The syringe 14 may also be considered part of the feeding set assembly 7. However, feeding set assemblies including more of fewer components than described herein are within the scope of the present invention.

In a preferred embodiment, the cassette shell 9 is made from a polymeric material such as polycarbonate. Referring to FIGS. 3 and 4, an insert 105 may be received in the cassette recess 6 in the housing 3 to aid in securing the cassette shell 9 and tube 45 in the cassette recess. The insert 105 may be positioned in the recess 6 such that the insert 105 is received in the back cavity of the cassette shell 9 when the cassette is attached to the housing 3. The insert 105 may comprise a pair of opposing first projections 107 disposed at an inlet side of the insert for receiving the inlet portion of the tube 45, and a pair of opposing second projections 109 disposed at an outlet side of the insert for receiving the outlet portion of the tube. Indicia 112 may be disposed on at least one of the second projections 109 indicating the direction of fluid flow in the tube 45. In the illustrated embodiment, the indicia 112 is in the form of an arrow.

Referring to FIGS. 1 and 7-11, a pump support is generally indicated at 16. The pump support 16 comprises a base 60 for supporting the pump support on a horizontal support surface such as a tabletop, and a syringe holder 62 attached to the base for securing the syringe 14 to the base. The syringe 14 and syringe holder 62 comprise the syringe assembly 12. The pump support 16 supports the syringe 14 relative to the pump 1 when the pump is mounted on the pump support. More particularly, and as will be explained in greater detail below, the pump support 16 is configured to orient the syringe in multiple angular orientations. Alternatively, the pump support 16 may be configured as a syringe stand such that the holder receives and supports the syringe 14 but does not also mount and/or support the pump 1.

The syringe 14 may be a conventional syringe including a barrel 18, which may be graduated, and a plunger 20 slidably received in the barrel. In the illustrated embodiment, the syringe 14 includes a female tip 24 including an external thread 26 and defining an outlet 28 and tip passage in communication with an interior of the barrel 18. The female tip 24 is centered about a longitudinal axis LA of the syringe 14. The syringe 14 may be of other configurations without departing from the scope of the present disclosure. For example, the syringe may have an eccentric tip such that the female tip is positioned off-center of the longitudinal axis of the syringe. Still other syringe configurations are envisioned within the scope of the disclosure.

Referring to FIGS. 1 and 9-11, syringe connector 30 attaches the syringe 14 to the inlet tubing 77 to fluidly connect the syringe to the inlet tubing. The syringe connector 30 comprises a one-piece, integrally formed, molded connector body, generally indicated 34. The connector body 34 includes a syringe-connecting portion 38 adapted to removably connect to the female tip 24 of the syringe 14, a tube-connecting portion 40 that receives an end of the inlet tubing 77 to fluidly connect an output of the syringe with the second attachment portion 75A of the inlet port 69 of the cassette 5, and a valve portion 41 receiving a valve or plug 47 and configured to purge the syringe after delivery of the feeding fluid. The syringe-connecting portion 38 includes a male component 42 configured to form a liquid-tight seal with the female tip 24 of the syringe 14 when inserted into the tip passage. An outer skirt 44 of the syringe-connecting portion 38 surrounds the male component 42 and includes an internal thread 46 configured to threadably mate with the external thread 26 of the female tip 24.

The syringe connector 30 defines air and enteral fluid passages 50, 52, respectively. The enteral fluid passage 52 fluidly connects the interior of the barrel 20 with the inlet tubing 77. The air passage 50 is configured to fluidly connect the inlet tubing 77 with atmosphere to purge the inlet tubing of fluid, as explained in more detail below. The enteral fluid passage 52 has a first portion 52a extending generally along an axis A1 of the connector body 34, through the male component 42 of the syringe-connecting portion 38. A second portion 52b of the enteral fluid passage 52 leading to the inlet tubing 77 extends through the tube-connecting portion 40 generally orthogonal to the first portion 52a and the axis A1 of the connector body. The air passage 50 has a first portion 50a extending generally along the axis A1 of the connector body 34, through the valve portion 41. A second portion 50b of the air passage 50 leading to the inlet tubing 77 extends through the tube-connecting portion 40 generally orthogonal to the first portion 50a and the axis A1 of the connector body. The second portion 50b of the air passage 50 is coincident with the second portion 52b of the enteral fluid passage 52 such that they occupy the same passage through the connector 30.

The valve 47 is received in the valve portion 41 of the syringe connector 30 and seals the air passage 50 from atmosphere. With the valve 47 received in the valve portion 41, normal operation of the pump 1 may be engaged whereby the rotation of the rotor 37 creates a vacuum in the barrel 20 of the syringe 14 for drawing fluid from the syringe. However, once all the fluid has been delivered from the syringe 14, there may still be some fluid left in the inlet tubing 77 that has not been pumped to the subject. In order to deliver this portion of the fluid, the valve 47 can be opened thereby communicating the air passage 50 with atmosphere. Atmospheric air is then allowed to flow into the air passage 50 and into the inlet tubing 77 forcing the fluid in the tubing through the line and to the subject. This ensures that all the enteral fluid in the syringe 14 is delivered to the subject. The valve 47 can then be closed for subsequent feedings. In one embodiment, the valve 47 comprises a 1-way check valve such as a duckbill valve that allows air into the connector 30 once a pressure difference between the interior of the connector and atmosphere reaches at least 8 psi. In one example, the valve 47 may open when the pressure difference reaches between about 8 and about 10 psi. In one embodiment, the rotor 37 is rotated to a position where the tube 45 is not occluded to allow the air to force the fluid past the rotor and to the subject. The body 34 of the syringe connector 30 may be broadly considered a valve housing including a valve 47 for purging the inlet tubing 77 of fluid.

Figure 12:
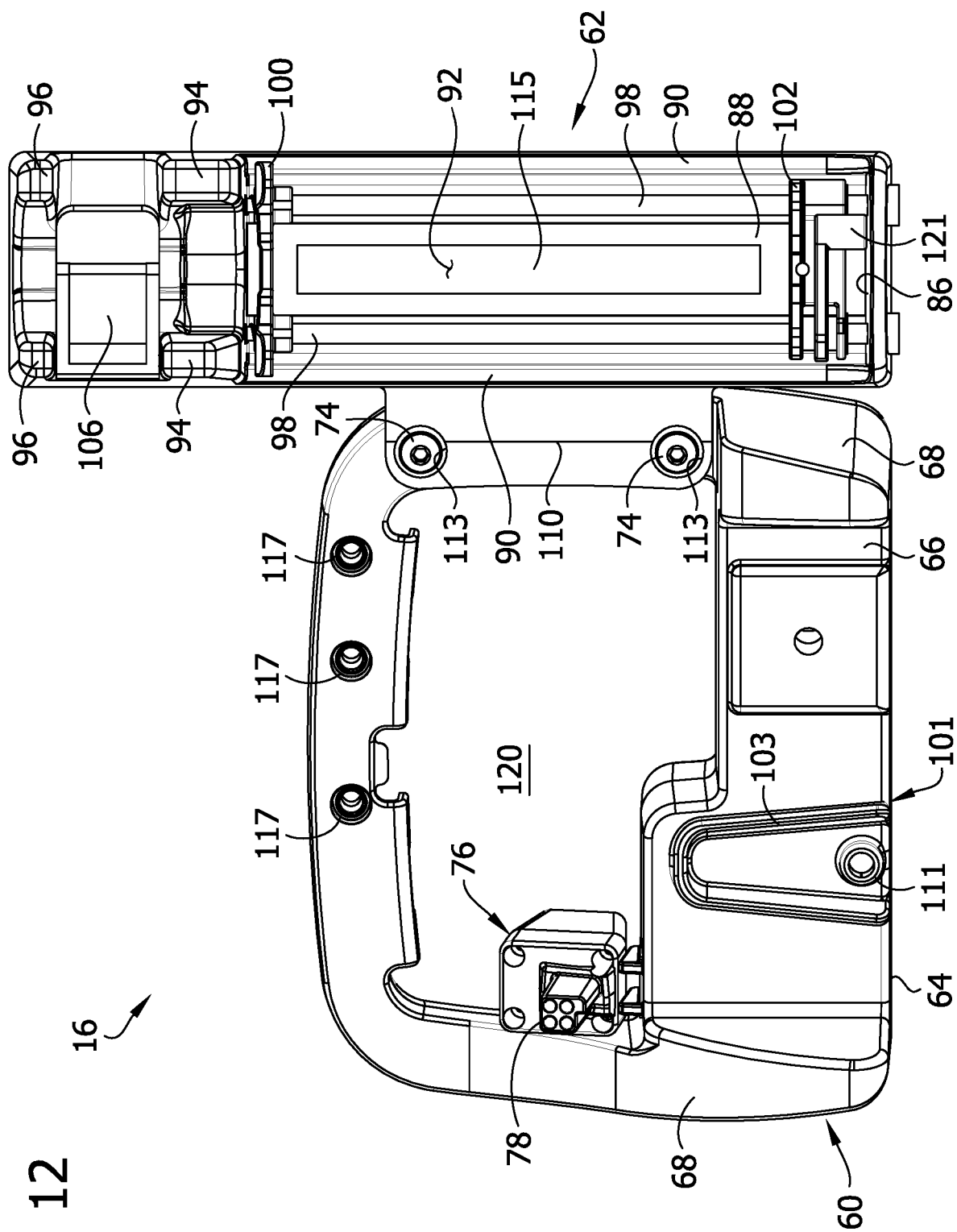
FIG. 12 is a front perspective view of the pump support.
Figure 13:
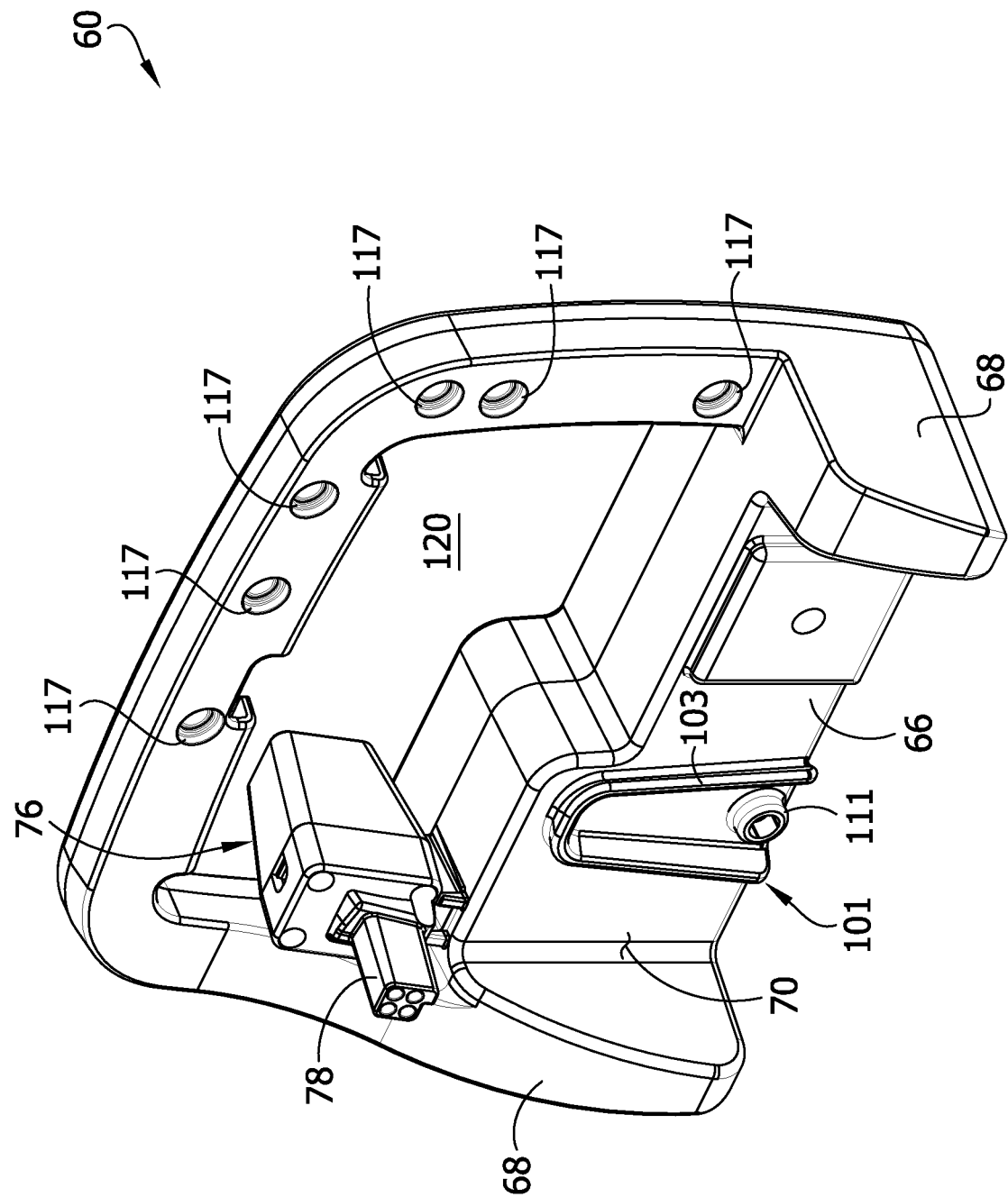
FIG. 13 is a front perspective view of a base of the pump support.
Figure 15:
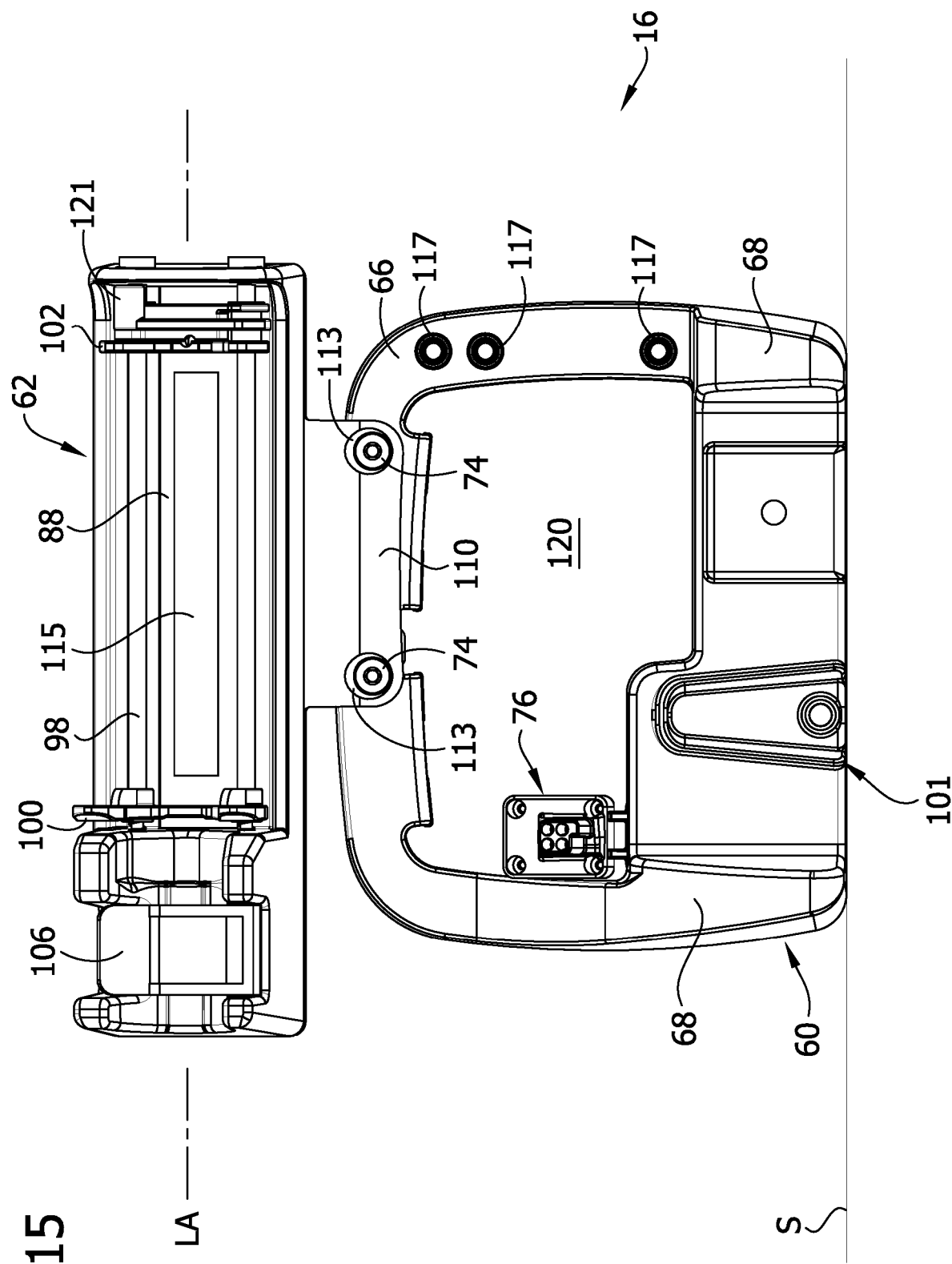
FIG. 15 is a front view of the pump support with the syringe holder in a horizontal orientation.
Figure 16:
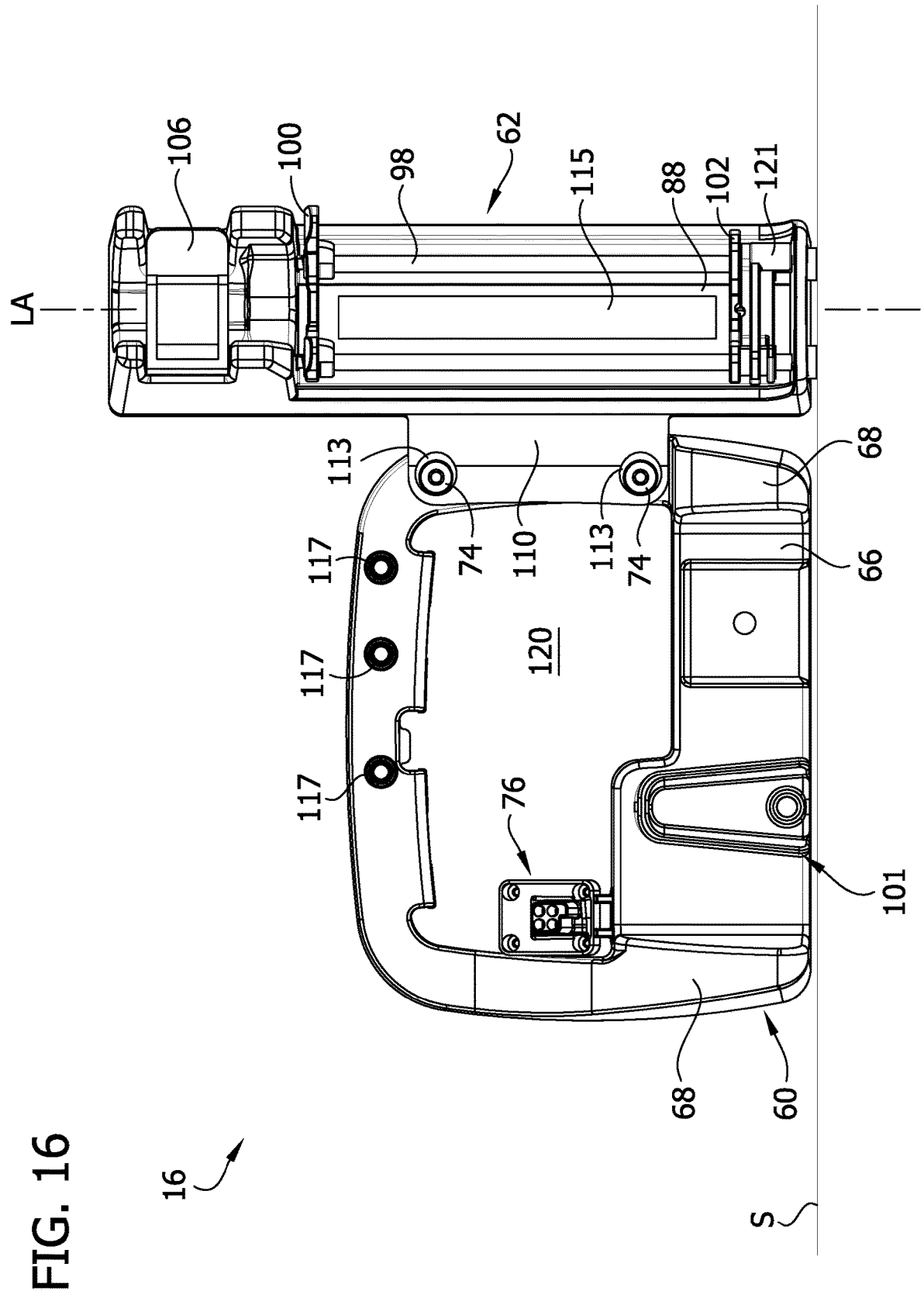
FIG. 16 is a front view of the pump support with the syringe holder in a vertical orientation.
Figure 18:
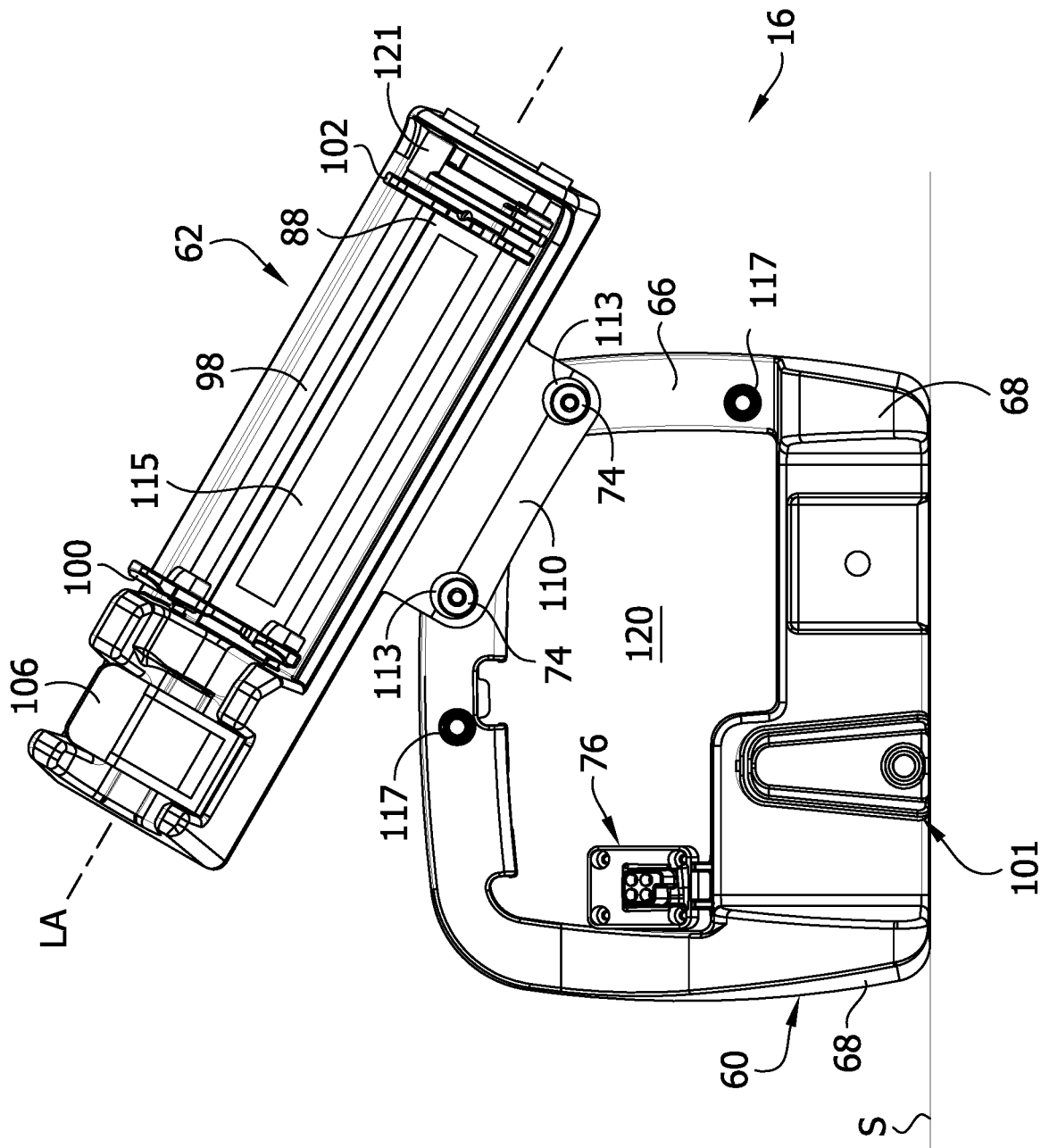
FIG. 18 is a front view of the syringe stand with the syringe holder in an angled orientation.

Referring to FIGS. 12 and 13, the pump support 16 comprises base 60 for supporting the pump support on a horizontal support surface such as a tabletop, and syringe holder 62 for securing the syringe 14 to the pump support. The holder 62 is attachable to the base 60 and selectively positionable relative to the base to orient the syringe 14 in a plurality of different positions on the pump support 16. For example, the pump support 16 is configured to orient the syringe 14 is a first configuration (FIG. 15) whereby the syringe is oriented in a generally horizontal orientation, and a second orientation (FIG. 16) whereby the syringe is oriented in a generally vertical orientation. The pump support 16 may also be configurable to orient the syringe 14 in a third configuration (FIG. 18) whereby the syringe 14 is oriented at an angle between the horizontal and vertical orientations. The pump support 16 may still also be configurable to orient the syringe in additional orientations between the horizontal and vertical orientations.

The base 60 has a flat bottom surface 64 for resting the base on a horizontal support surface. Thus, the base 60 itself is not configured to change its angular position with respect to a horizontal axis when resting on a horizontal support surface. A back wall 66 extends upward from the bottom surface 64 and mounts the pump 1 to the base 60. A pair of side walls 68 extend laterally from the back wall 66 opposing opposite sides of the pump 1 when the pump is mounted to the base 60. The back wall 66 and side walls 68 together define a receiving space 70 for the pump 1. A mount 101 may be disposed on the back wall 66. In the illustrated embodiment, the mount 101 has a rounded triangular or arched shape and includes a mounting flange 103 that diverges on opposite sides of the mount. The mounting flange 103 of the mount 101 may be configured to slidingly engage a groove 136 (FIG. 4A) formed in a back surface of the pump 1 to mount the pump to the base 60. A post 111 may be disposed on the back wall 66 within the perimeter of the mount 101 and may have a receptacle for receiving a retainer (not shown) for locking the pump 1 to the base 60. A cutout 120 in the back wall 66 forms a handle on the base 60 for carrying the pump support 16. The back wall 66 attaches to the holder 62 to locate the holder relative to the base 60. In the illustrated embodiment, multiple holes 117 are formed in the back wall 66 and are configured to receive fasteners 74 for attaching the holder 62 to the base 60. It will be understood that other means for attaching the holder 62 to the base 60 may be utilized without departing from the scope of the disclosure.

Figure 4A:
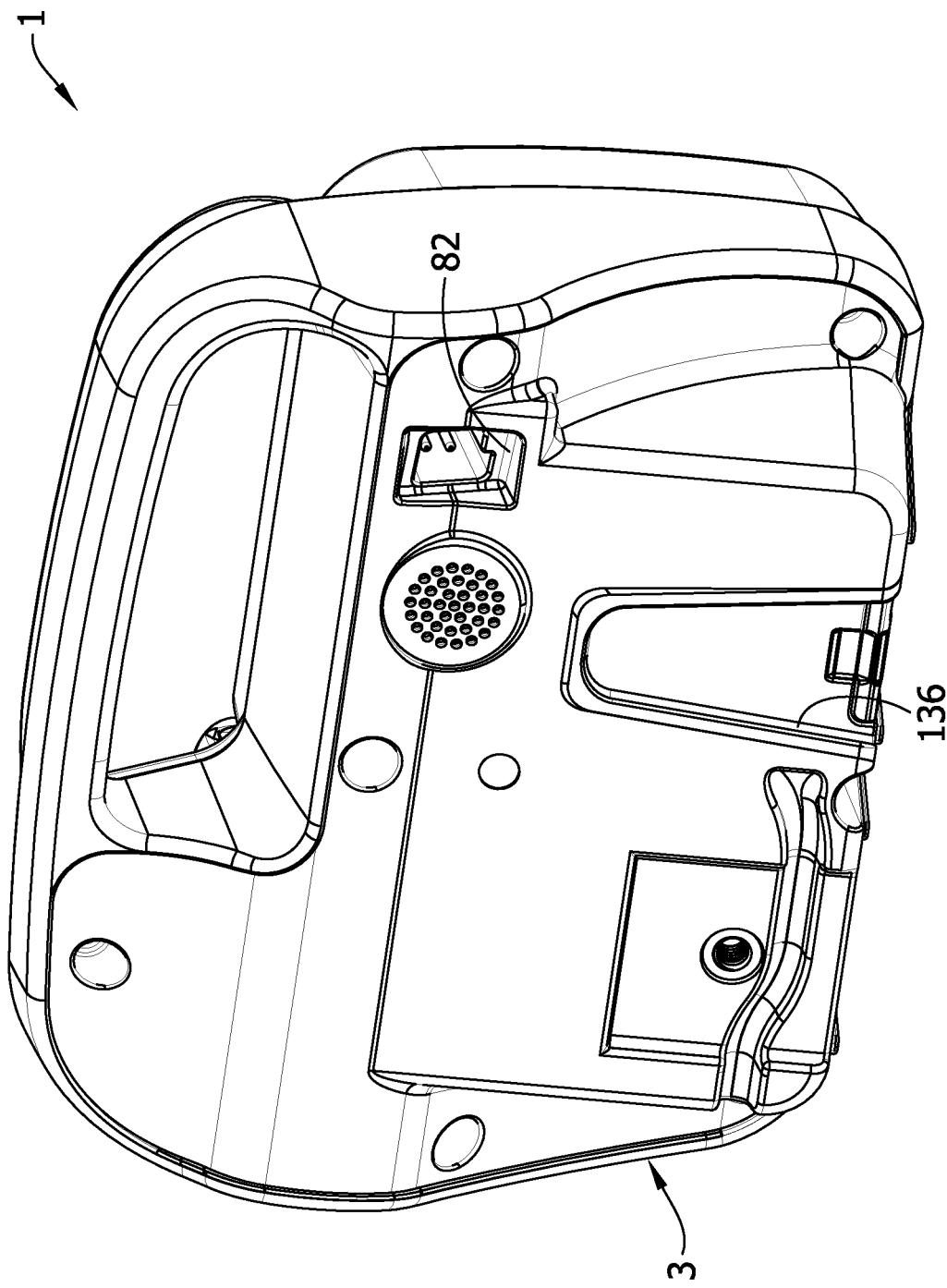
FIG. 4A is a rear perspective view of the enteral feeding pump.

A pass-thru connector 76 is formed on and extends through the back wall 66 in the cutout 120. The pas-thru connector 76 includes a plug 78 that extends forwardly on the connector 76 and into the receive space 70. A port 80 is formed in a reward side of the connector 76 and extends at least partially through the connector. The port 80 is in electrical communication with the plug 78 such that power and data can be transferred from the port to the plug and thus through the connector 76. The plug 78 is configured to connect to a port 82 on the back of the pump 1 (FIG. 4A). The port 80 on the base 60 is configured to receive a plug of a power cord (now shown) such that power from the power cord is transferred to both the pump support 16 and the pump 1 when the plug 78 of the pump support is received in the port 82 on the pump 1. In the illustrated embodiment, the pass-thru connector 76 is formed integrally with the base. However, the pass-thru connector 76 could be formed separately from the base 60 and suitably attached to the base. Additionally, a USB or other suitable connector (not shown) may be provided on the base 60. The USB connector is configured to transfer data to the pump support 16 and pump 1. For example, software updates may be communicated to the pump support 16 and pump 1 through the USB connector. In one embodiment, the USB connector is formed as part of the pass-thru connector 76.

Figure 7:
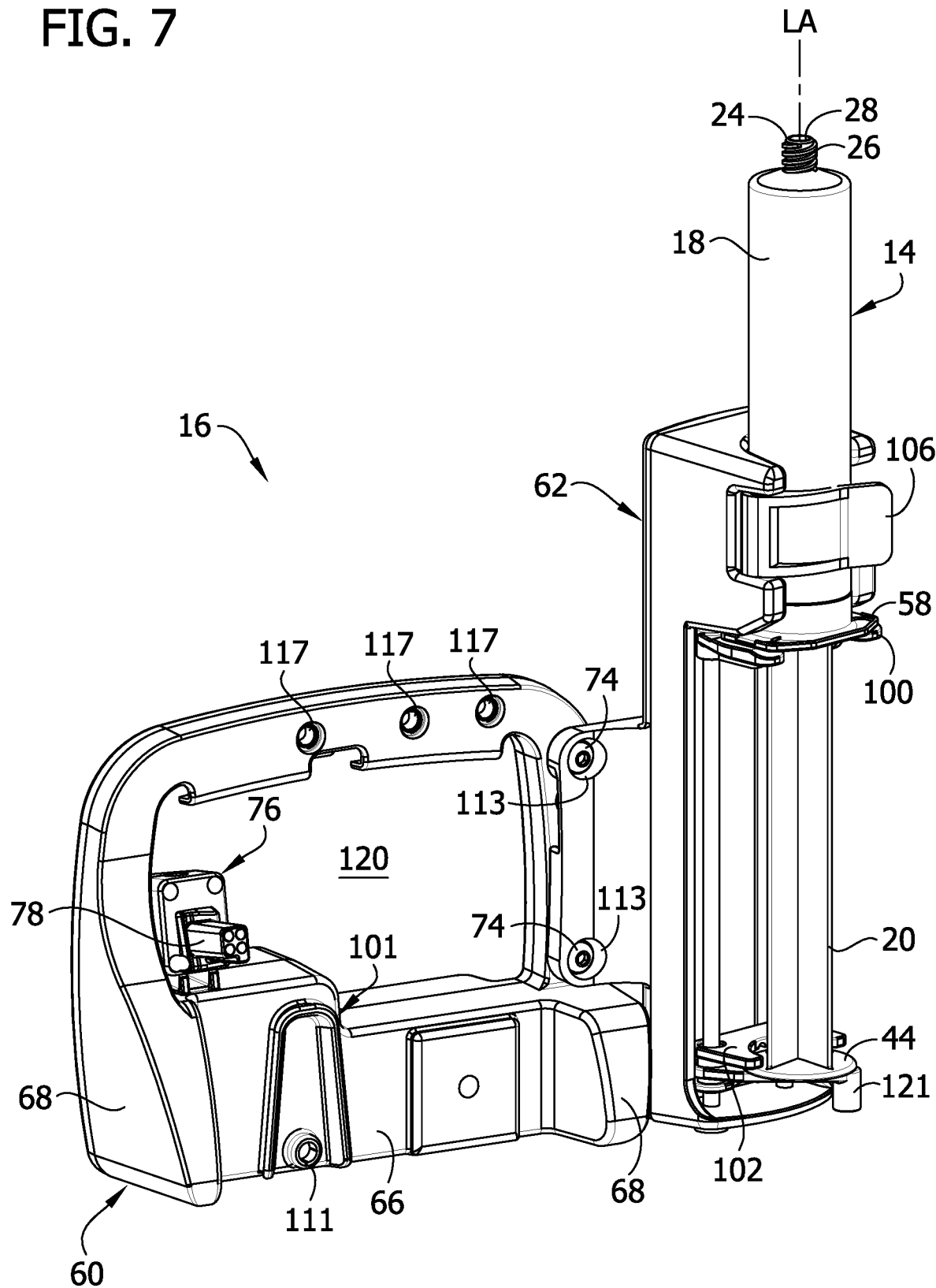
FIG. 7 is a front perspective view of a pump support and syringe of the feeding set assembly.
Figure 8:
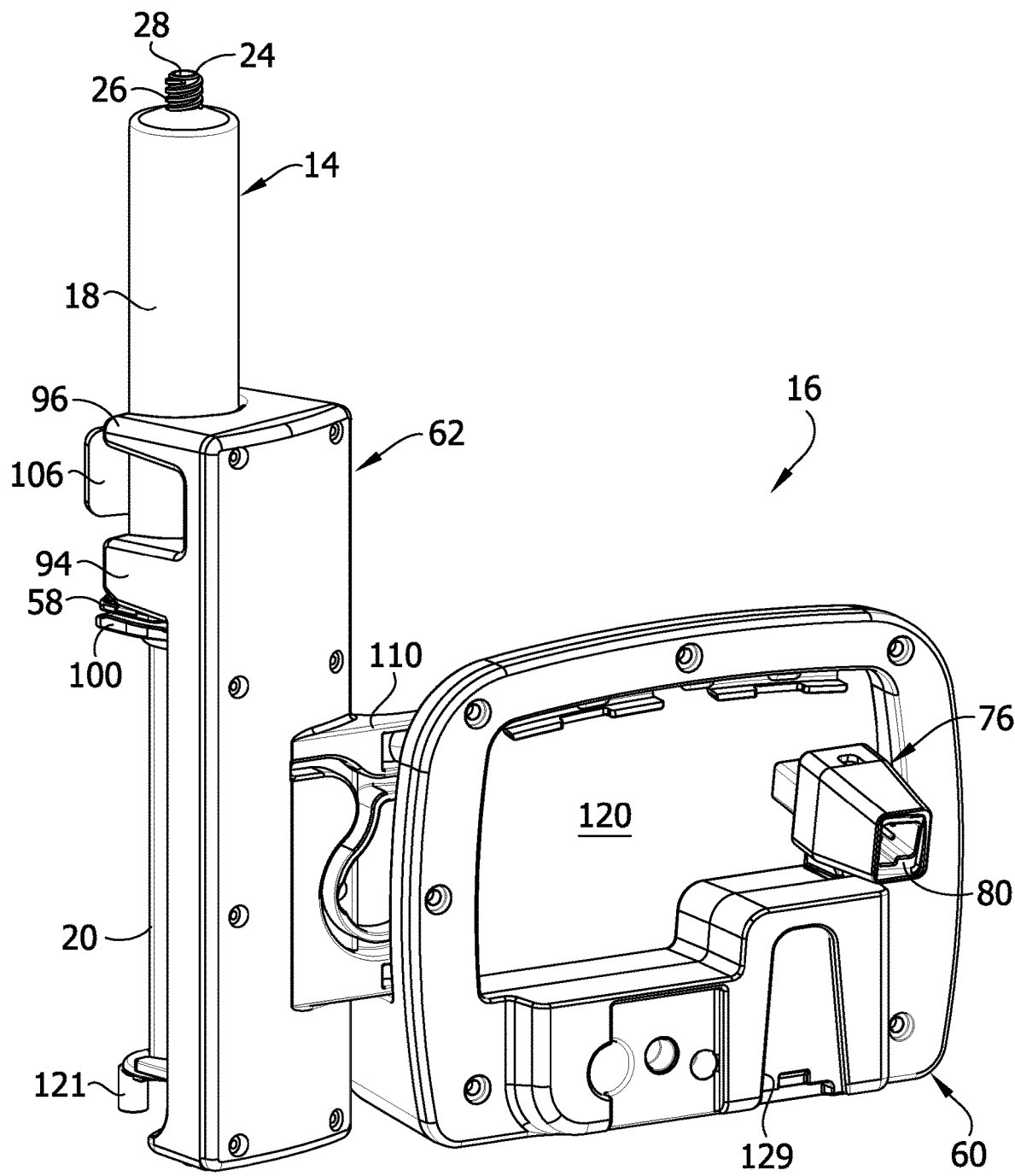
FIG. 8 is a rear perspective view of the pump support and syringe.
Figure 9:
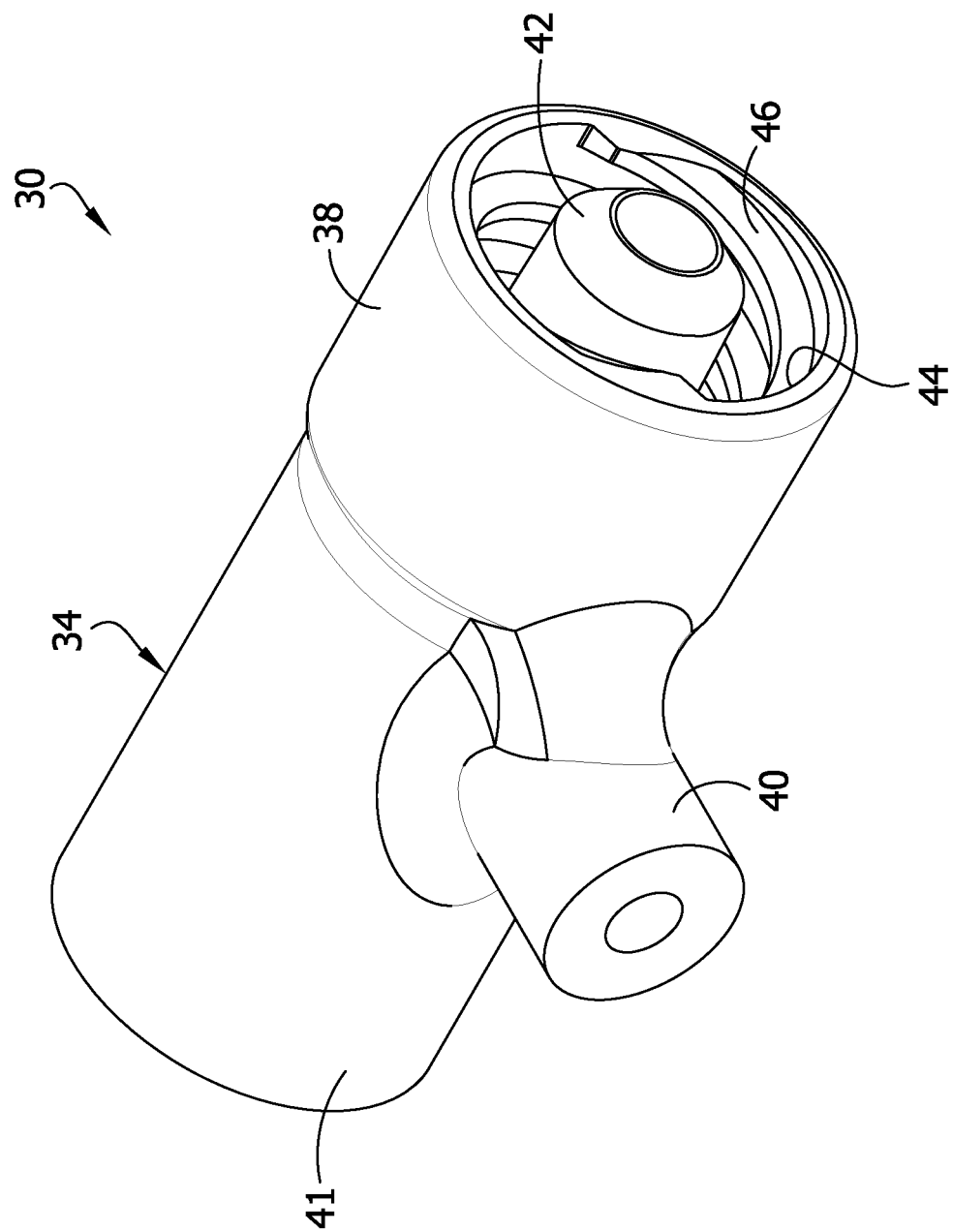
FIG. 9 is a perspective of a syringe connector of the feeding set assembly.
Figure 10:
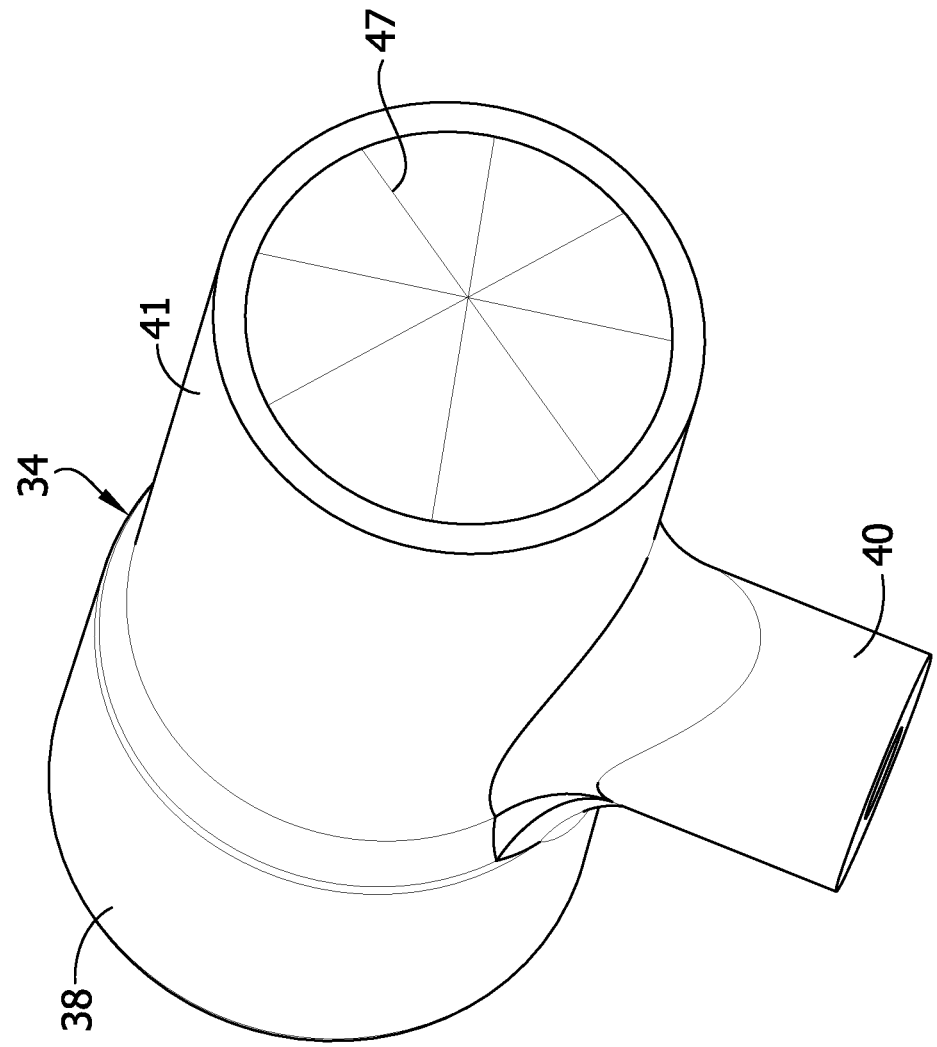
FIG. 10 is another perspective of the syringe connector.
Figure 11:
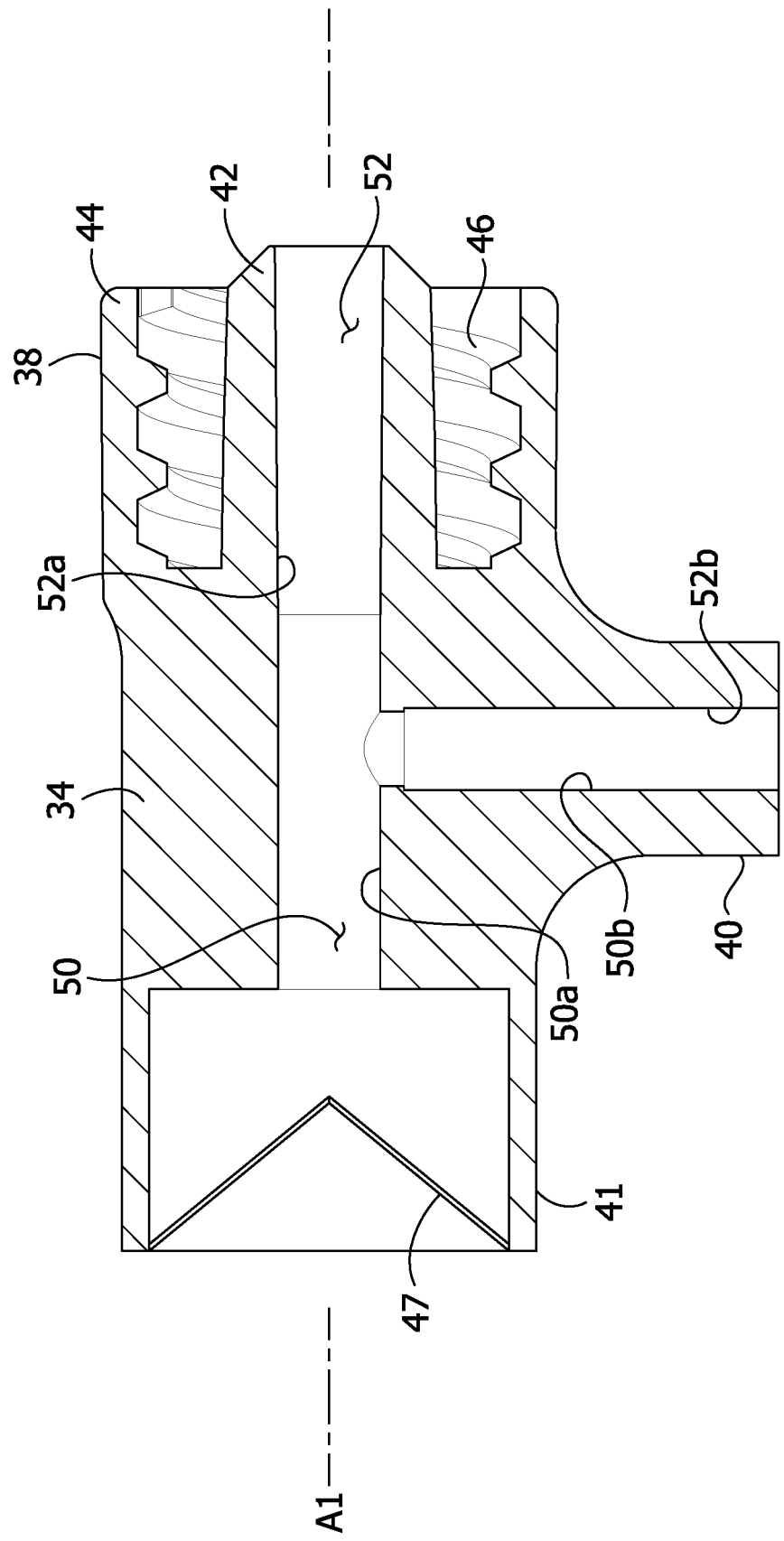
FIG. 11 is a section of the syringe connector.
Figure 14:
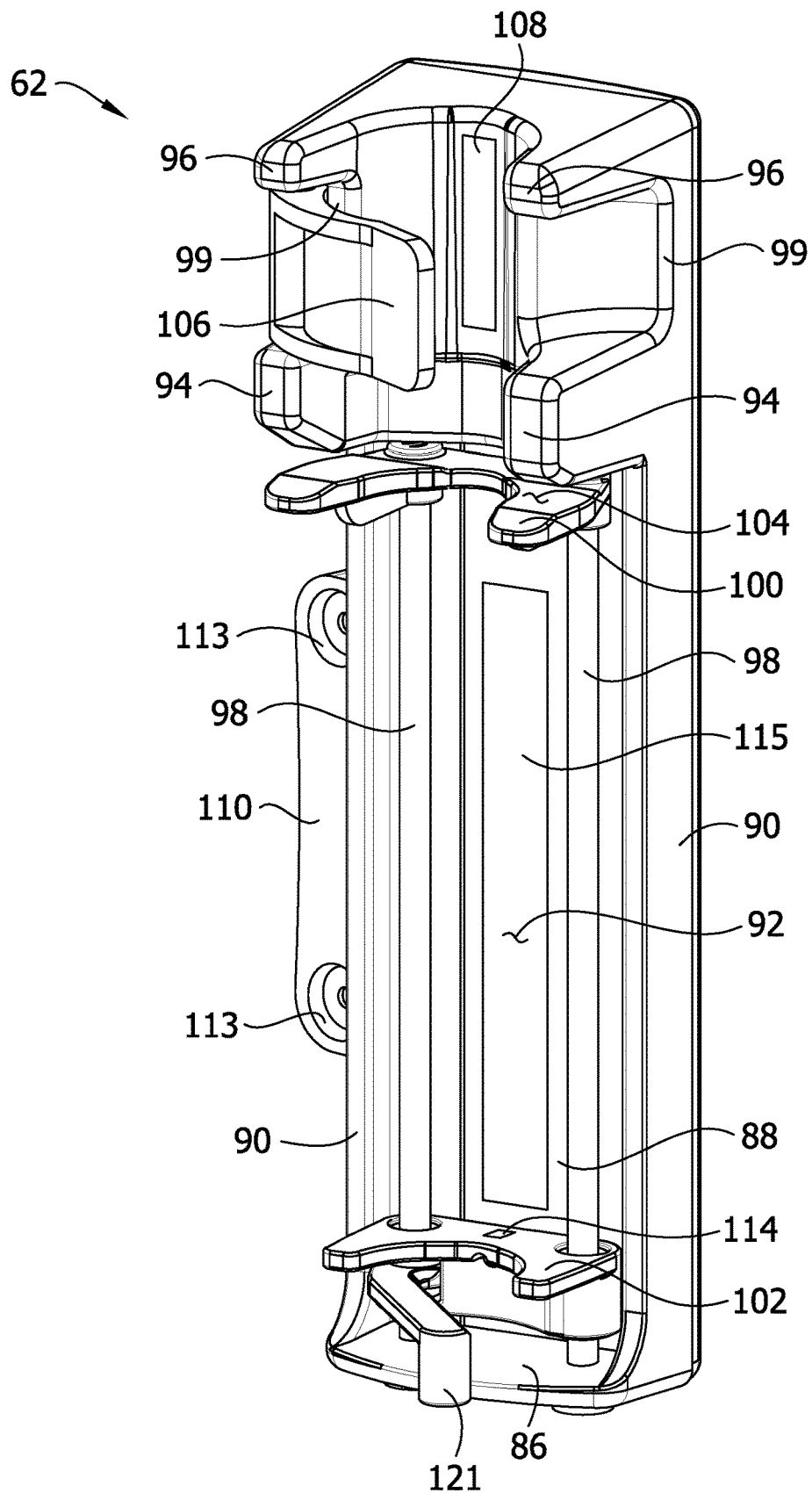
FIG. 14 is a front perspective view of a syringe holder of the pump support.

Referring to FIGS. 12 and 14, the syringe holder 62 includes a floor 86, a rear wall 88 extending from the floor, and opposing side walls 90 extending laterally from the rear wall and away from the floor. The floor 86, rear wall 88, and side walls 90 together define a receiving space 92 for at least a portion of the syringe 14. A first pair of flanges 94 extend from respective side walls 90 of the holder 62 near a top of the holder. Each side wall 90 has a recessed portion 99 above the flange 94 forming a second pair of flanges 96 longitudinally spaced from the first pair of flanges 94. A portion of the barrel 18 of the syringe 14 is received between the first pair of flanges 94 and between the second pair of flanges 96. The flanges 94, 96 prevent lateral movement of the barrel 18 in the holder 62 along an axis parallel to the rear wall 88. A pair of rails 98 extend between the floor 86 and the first pair of flanges 94. A U-shaped plate 100 is fixedly disposed at a top end of the rails 98, and a U-shaped slide 102 is disposed around a bottom end of the rails and configured to move or slide along the rails. A gap 104 is formed between the first pairs of flanges 94 and the U-shaped plate 100. The gap 104 is configured to receive a flange 58 of the barrel 18 of the syringe 14 (FIG. 7). The length of the gap 104 is slightly larger than a thickness of the flange 58. Thus, the flange 58 is held fixed between the flanges 94 and the plate 100 thereby fixing the barrel 18 against longitudinal movement within the holder 62. Further, when the syringe 14 is received in the holder 62, a flange 44 of the plunger 20 is held between a lever 121 and the slide 102. For example, the lever 121 is actutable to rotate the lever to the left as shown in FIG. 14 to slide the lever down the rail 98 to provide clearance for the plunger flange 44. The U shape of the slide 102 and plate 100 are sized and shaped to receive a rod of the plunger 20 therein. The lever 121 can then be rotated back to the right to slide the lever up the rail 98 to secure the plunger flange 44 to the slide 102. As will be explained in greater detail below, fluid being drawn from the barrel 18 of the syringe 14 causes the plunger 20 to move away from the floor 86. The movement of the plunger 20 is guided by the slides 102 on the rails 98 so that the plunger moves along a substantially linear axis. Alternatively, the syringe holder could be configured to fix the longitudinal position of the plunger 20 and allow the barrel 18 to move relative to the plunger when fluid is drawn from the barrel.

A door or gate 106 is pivotably attached between one of the first pair of flanges 94 and one of the second pair of flanges 96 and moveable between an open position to allow the syringe 14 to be received in the receiving space 92, and a closed position for retaining the syringe in the receiving space. A sensor 108 (FIG. 14) may be provided on the holder 62 to detect the position of the door 106 once it is moved the closed position. Based on the position of the door 106, a determination of the size of the syringe 14 can be made. For instance, a controller 72 (FIG. 19) in the pump 1 may initiate a prompt requiring confirmation by a user in response to the door 106 being located at a predetermined position indicating the size of the syringe 14 as a preprogrammed size stored within a memory 93. Alternatively, the controller 72 may automatically determine the size of the syringe 14 based on the position of the door 106. A connection arm 110 extends from one of the side walls 90 and is configured to attach the holder 62 to the base 60. In particular, the connection arm 110 includes multiple holes 113 corresponding to the holes 117 in the back wall 66 of the base 60 so the fasteners 74 can be received through the holes to attach the holder 62 to the base.

Referring to FIGS. 1 and 14, a position sensor 115 may be attached to the rear wall 88 to detect movement of the plunger 20. In the illustrated embodiment, the position sensor 115 comprises a linear resistive potentiometer. A contact 114 of the potentiometer 115 is disposed on a movable portion of the holder 62, such as the slide 102, so that movement of the slide causes the contact to move along the potentiometer 115. Because the barrel 18 is held fixed in the holder 62, as fluid is withdrawn from the barrel, the plunger 20 will move into the barrel. The flange 44 of the plunger 20 engages the slide 102 as the plunger moves into the barrel 18 causing the slide to move along the rails 98. Therefore, in this embodiment, movement of the contact 114 represents the movement of the plunger 20 relative to the barrel 18 and holder 62 caused by the feeding fluid being drawn out of the syringe 14. Stated another way, the movement of the contact 114 corresponds to the distance which the plunger 20 has advanced into the barrel 18. Since the cross-sectional area of the internal cavity of the barrel 18 is known from the detection of the syringe size, the potentiometer 115 can be calibrated so that the movement of the contact 114 indicates the volume of fluid expelled from the syringe 14. In particular, by knowing the inner diameter of the barrel 18 of the syringe 14, in combination with the distance the slide 102/plunger 20 has moved, the volume of fluid delivered from the syringe 14 can be determined. The potentiometer 115 may be electrically connected to the controller 72 for receiving position signals from the potentiometer 115 indicating the movement of the slide 102. The controller 72 may be located in the pump 1 or may be located remote from the pump 1 and in communication with the pump 1. For example, the controller 72 may be located in the pump support 16. In the embodiment where the plunger 20 is held fixed and the barrel 18 moves relative to the plunger, the movement of the contact represents the movement of the barrel 18.

Other position sensors are also envisioned without departing from the scope of the disclosure. For example, a linear magneto resistive potentiometer (not shown) may be used. In this embodiment, a magnetic contact can be attached to the slide 102, or alternatively attached to a structure attached to the plunger 20, to gauge the movement of the slide/plunger. The magnetic contact being attached to the plunger would require syringes that have the magnetic contact to be used with the pumping system. Still further, an inductive position sensor (not shown) could be used. In still another embodiment, a camera (not shown) could be used to monitor the movement of the plunger 20. In this embodiment, the movement of any point on the syringe 14 (e.g., plunger 20) can be tracked using image analysis software in communication with the camera. The size of the syringe 14 can also be automatically detected using the camera and image software. In still another embodiment, a foil sensor or nonmagnetic sensor may be employed. In further embodiments, fluid delivery amounts could be determined by weight detection. The examples of position sensing devices is not exhaustive of those which fall within the scope of the present invention.

The exemplary feeding set assembly 7 may be used for enteral feeding of neonates to achieve metered fluid delivery using the enteral feeding pump 1. In such a method, the enteral liquid is drawn into the syringe 14 by pulling back on the plunger 20. The amount of enteral liquid may be measured using graduation markings on the barrel 18 of the syringe 14. After filling the syringe 14 with the proper amount of enteral liquid, the syringe connector 30 can be attached to the syringe tip 24, such as by threading the syringe-connecting portion 38 onto the tip. The tube-connecting portion 40 can also be connected to the inlet tubing 77. Prior to attaching the cassette 5 to the pump housing 3, the inlet tubing 77 can be connected to the outlet port 69, and the outlet tubing 83 may be attached to the outlet port 71 of the cassette 5.

Figure 2:
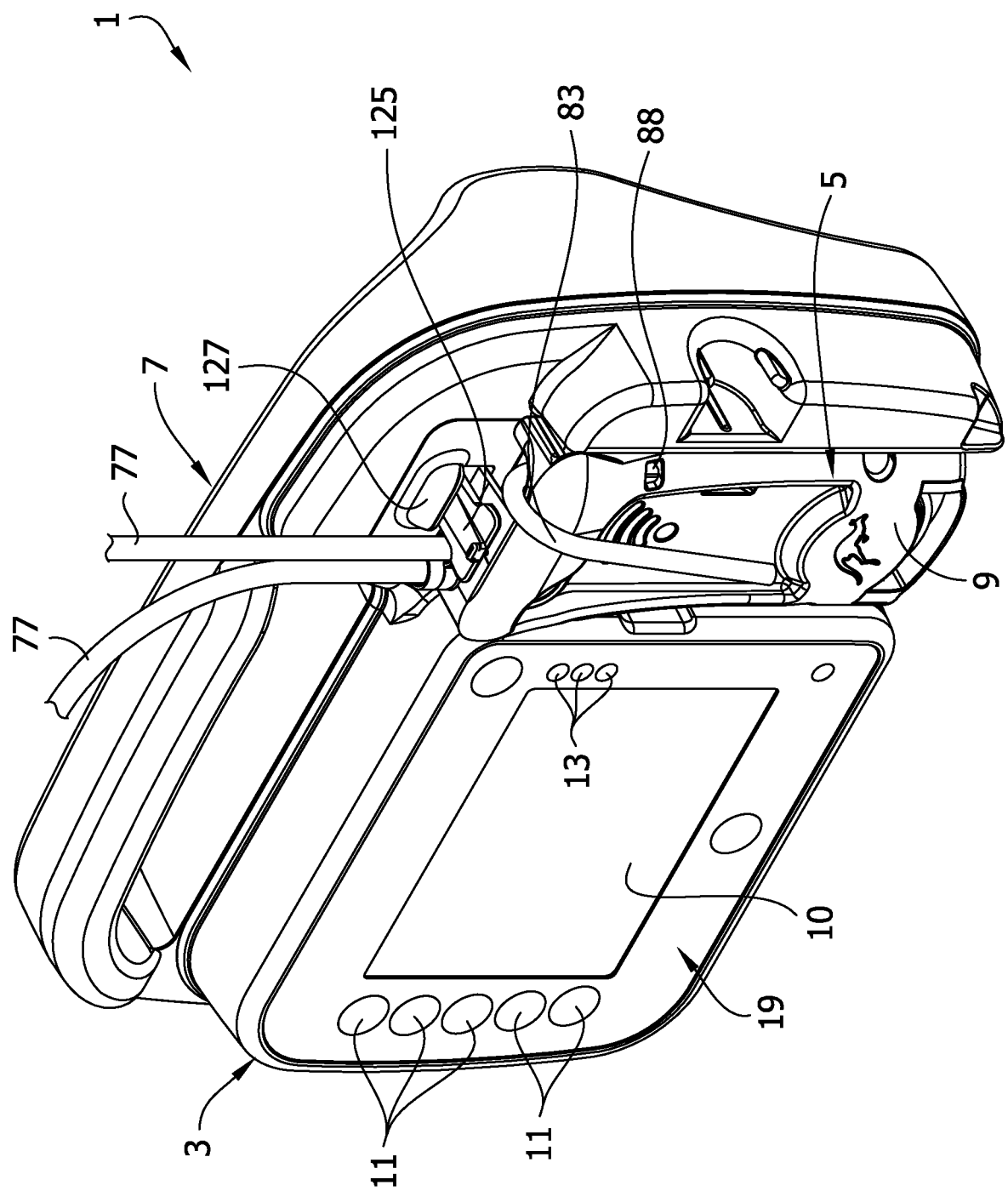
FIG. 2 is an fragmentary, perspective view of the feeding system including the enteral feeding pump, and part of the feeding set assembly.

To attach the cassette 5 to the pump housing 3, one or more pins or raised projections 119 (FIG. 5) at the bottom 59 of the cassette body 51 of the cassette shell 9 may be inserted in slots 124 (FIGS. 3 and 4) at the bottom of the recess 6 in the housing 3. The engagement between the raised projections 119 and slots 124 generally locates the cassette shell 9 on the housing 3. The cassette body 51 can then be rotated up until ledges 123 on a tab 125 at the top 57 of the cassette body are captured by a catch 127 at the top of the recess 6 (FIGS. 2 and 4). To detach the cassette 5 from the pump housing 3, the tab 125 can be depressed to disengage the ledges 123 from the catch 127. Once the cassette 5 is attached to the pump housing 3, the tube 45 is positioned for engagement by the rollers 43 of the pump 1.

Figure 17:
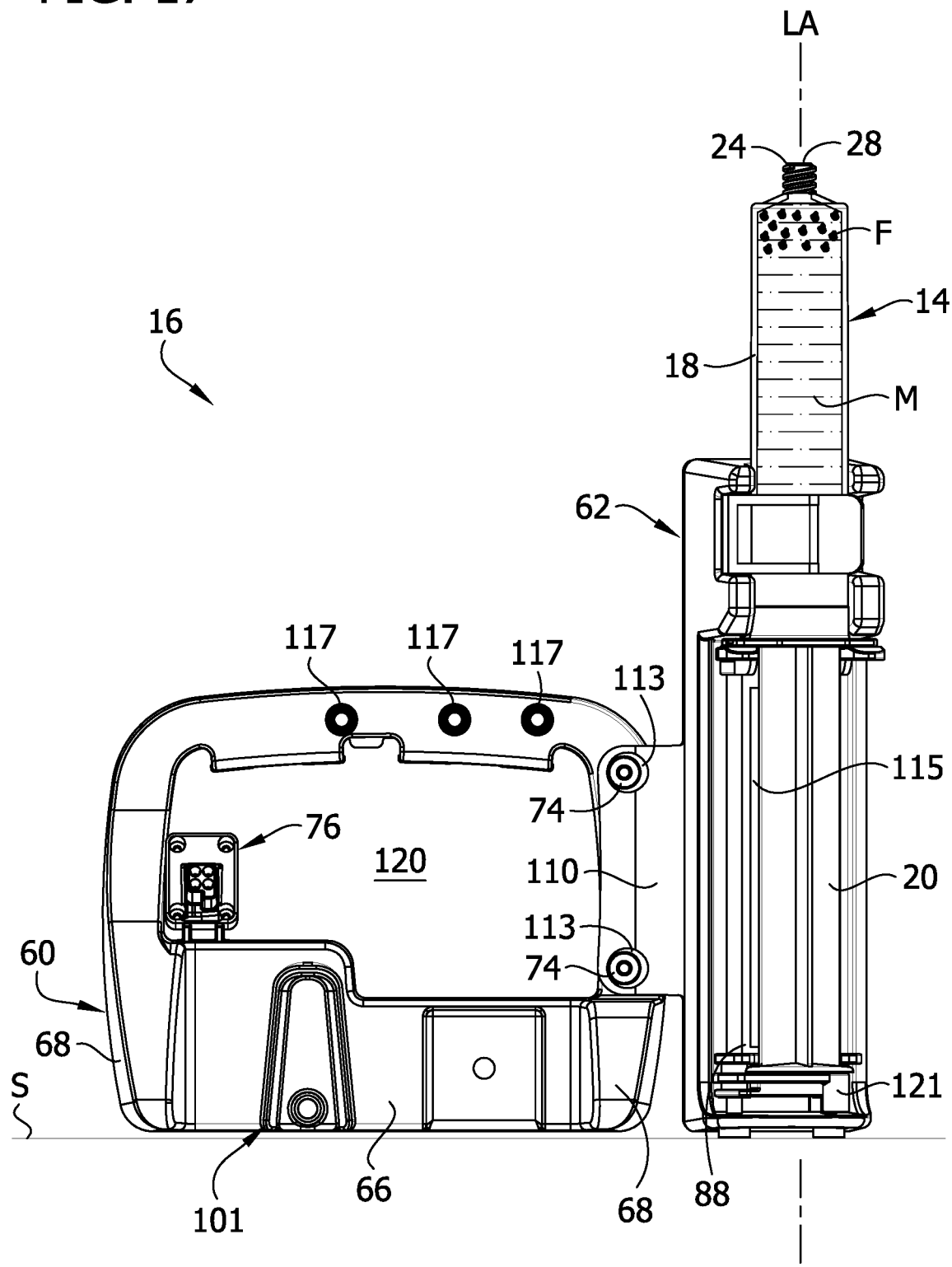
FIG. 17 is the front view of FIG. 16 with the syringe loaded in the syringe holder and schematically showing breast milk in the syringe.

The pump support 16 is configurable to place the syringe holder 62 in a plurality of different angular orientations while the pump 1 and base 60 of the pump support are supported in a horizontal orientation on a support surface S in order to place the syringe 14 received in the syringe holder in a corresponding angular orientation. Orienting the syringe 14 in a particular orientation may be advantageous for delivering a preferred nutrient within a volume of fluid in the syringe earlier in a feeding cycle. In one embodiment, the syringe 14 is selectively positionable in a horizontal orientation (FIG. 15) whereby the longitudinal axis LA of the syringe is oriented generally parallel to a horizontal axis when the syringe is received in the holder 62. This is done by attaching the connection arm 110 of the holder 62 to the back wall 66 of the base 60 in a first attachment position aligning the holes 113 in the connection arm with the holes 117 in the back wall in a first alignment orientation. In one embodiment, the syringe 14 is selectively positionable in a vertical orientation (FIG. 16) whereby the longitudinal axis LA of the syringe is oriented generally parallel to a vertical axis such that the tip 24 of the syringe is facing upward when the syringe is received in the holder 62 (FIG. 17). This is done by attaching the connection arm 110 of the holder 62 to the back wall 66 of the base 60 in a second attachment position, different from the first attachment position, aligning the holes 113 in the connection arm with the holes 117 in the back wall in a second alignment orientation. If the nutritional liquid held in the syringe 14 is breast milk M for example, by orienting the tip 24 of the syringe upward, natural separation of the contents of the breast milk M will cause any fat F within the milk M to rise to the top of the mixture, thereby locating the fat F closest to the outlet 28 of the syringe 14 relative to the non-fat liquid portion of the breast milk. Therefore, the fat F, which is the most important part of the milk M for the infant, will be delivered to the infant first. This will not occur when the syringe 14 is arranged so that the barrel 18 is oriented horizontally. In this orientation, the fat F of the breast milk M tends to accumulate at the top of the barrel 18, away from the tip 24 so that in a horizontal orientation the watery content of the milk M is delivered first. Often neonates can tolerate only very small quantities of milk at a given feeding. Thus, it is important that the neonate receives as much fat as possible and as soon as possible in a feeding. It is envisioned that preferred nutrients other than fat may be preferentially delivered with the syringe 14 positioned in the tip up vertical angular orientation. For example, vitamins and/or minerals within a nutritional liquid may be preferentially delivered in this angular orientation.

The pump support 16 is also configured to orient the syringe 14 in other angular orientations. In one embodiment, the syringe 14 is selectively positionable in an angled orientation (FIG. 18) whereby the longitudinal axis LA of the syringe is disposed at an angle to the vertical and horizontal axes such that the tip 24 of the syringe is facing upward at an angle when the syringe is received in the holder 62. This is done by attaching the connection arm 110 of the holder 62 to the back wall 66 of the base 60 in a third attachment position, different from the first and second attachment positions, aligning the holes 113 in the connection arm with the holes 117 in the back wall in a third alignment orientation. Orienting the syringe 14 in this manner also allows for the natural separation of the contents of breast milk in the syringe. In the illustrated embodiment, the syringe is oriented at about a 40 degree angle with respect to the horizontal axis. However, the syringe 14 could be positioned at other angles without departing from the scope of the disclosure. In one embodiment, the syringe 14 can be oriented at an angle between about 20 and about 60 degrees with respect to the horizontal axis. In one embodiment, the syringe 14 can be oriented at an angle between about 20 and about 40 degrees with respect to the horizontal axis.

In one embodiment, the pump support 16 can be attached to a vertical support such as an IV pole to orient the syringe 14 in a second vertical orientation whereby the longitudinal axis LA of the syringe is generally parallel to the vertical axis such that the tip 24 of the syringe is facing downward. For example, the pump support 16 can be configured in any of the angular orientations of FIGS. 15, 16, and 18 and mounted on the IV pole via a mount 129 on the back of the pump support. The pump support 16 can then be manipulated (e.g., rotated or turned) to orient the syringe 14 such that it extends vertically with the tip 24 pointing down. Orienting the syringe 14 in this manner facilitates delivery of fortifier in the syringe 14 to an infant. This is because the nutrients in the fortifier will sink to the bottom of the barrel 20 of the syringe 14. Thus, if the tip 24 of the syringe 14 is located at the bottom of the syringe 14, the nutrients from the fortifier will be delivered first. Additionally, with the pump support 16 configured in any of the angular orientations of FIGS. 15, 16, and 18 and mounted on a vertical support, the pump support can be manipulated to orient the syringe 14 in any desired angular orientation.

In one embodiment, the pump support 16 is configured such that the orientation of the syringe holder 62 cannot be changed while the pump 1 is received on the pump support. Thus, the syringe holder 62 must remain in a selected orientation once operation of the pump 1 has begun. Therefore, changing the orientation of the syringe holder 62 requires removal of the pump 1 from the pump support 16 and a tool to detach the syringe holder 62 from the base 60 to reposition the syringe holder as desired. In one embodiment, the pump support 16 must be returned to a hospital biotech department or to the manufacturer to change the position of the syringe holder 62.

Figure 20:
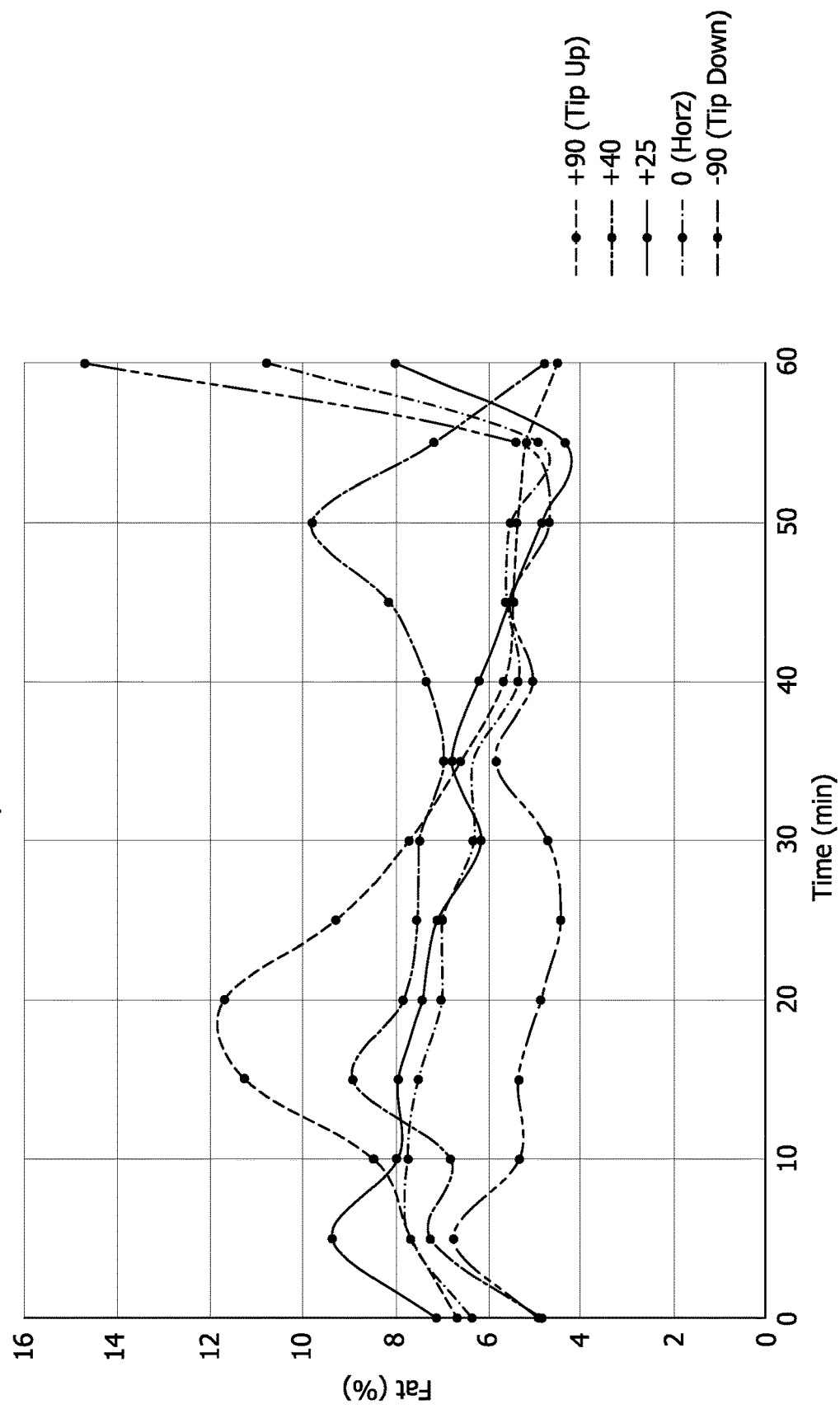
FIG. 20 is a graph showing a percentage of fat delivered at a given time over a delivery cycle of breast milk for various syringe orientations.
Figure 21:
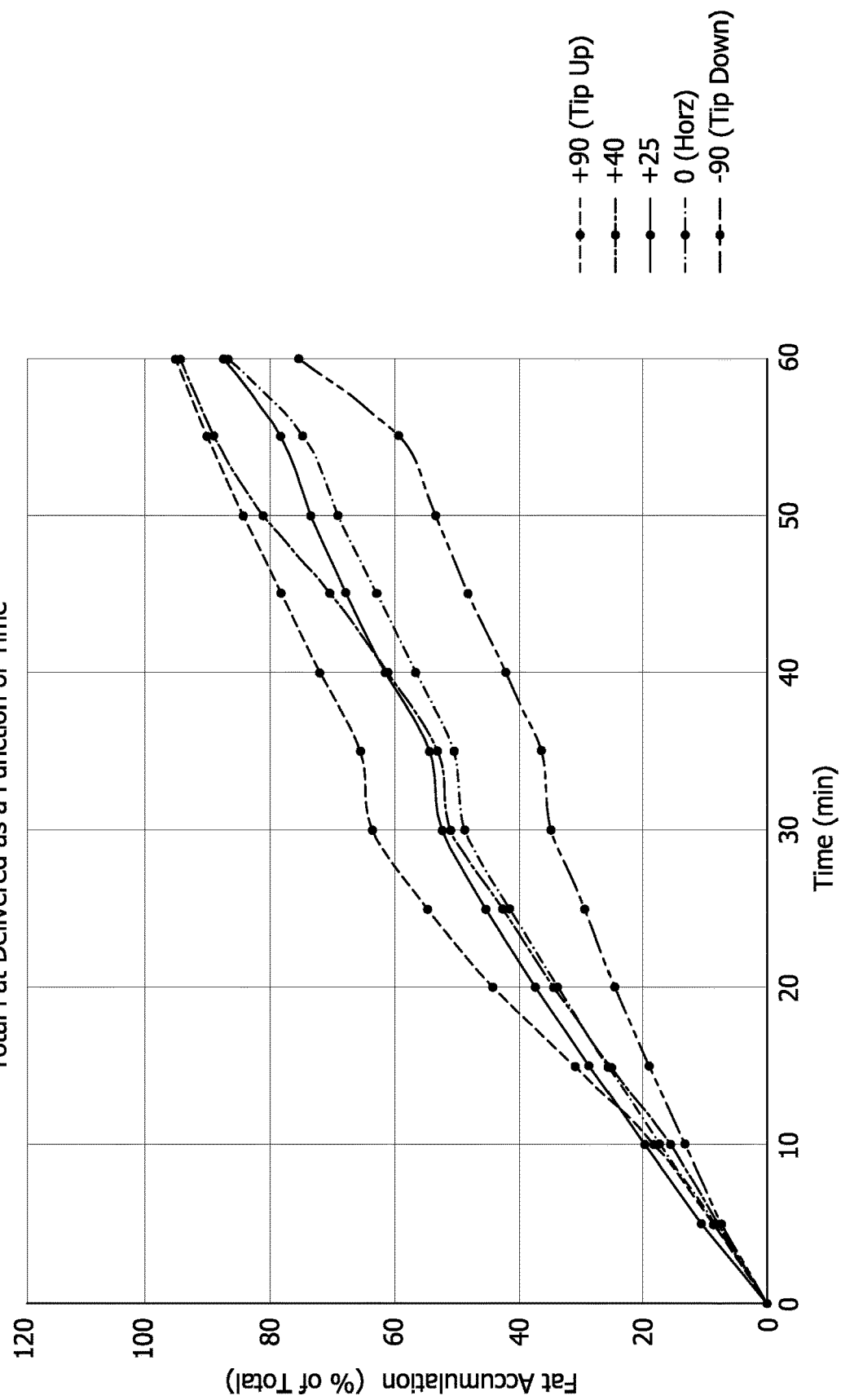
FIG. 21 is a graph showing a percentage of total accumulated fat delivered over time for a delivery cycle of breast milk for various syringe orientations.
Figure 22:
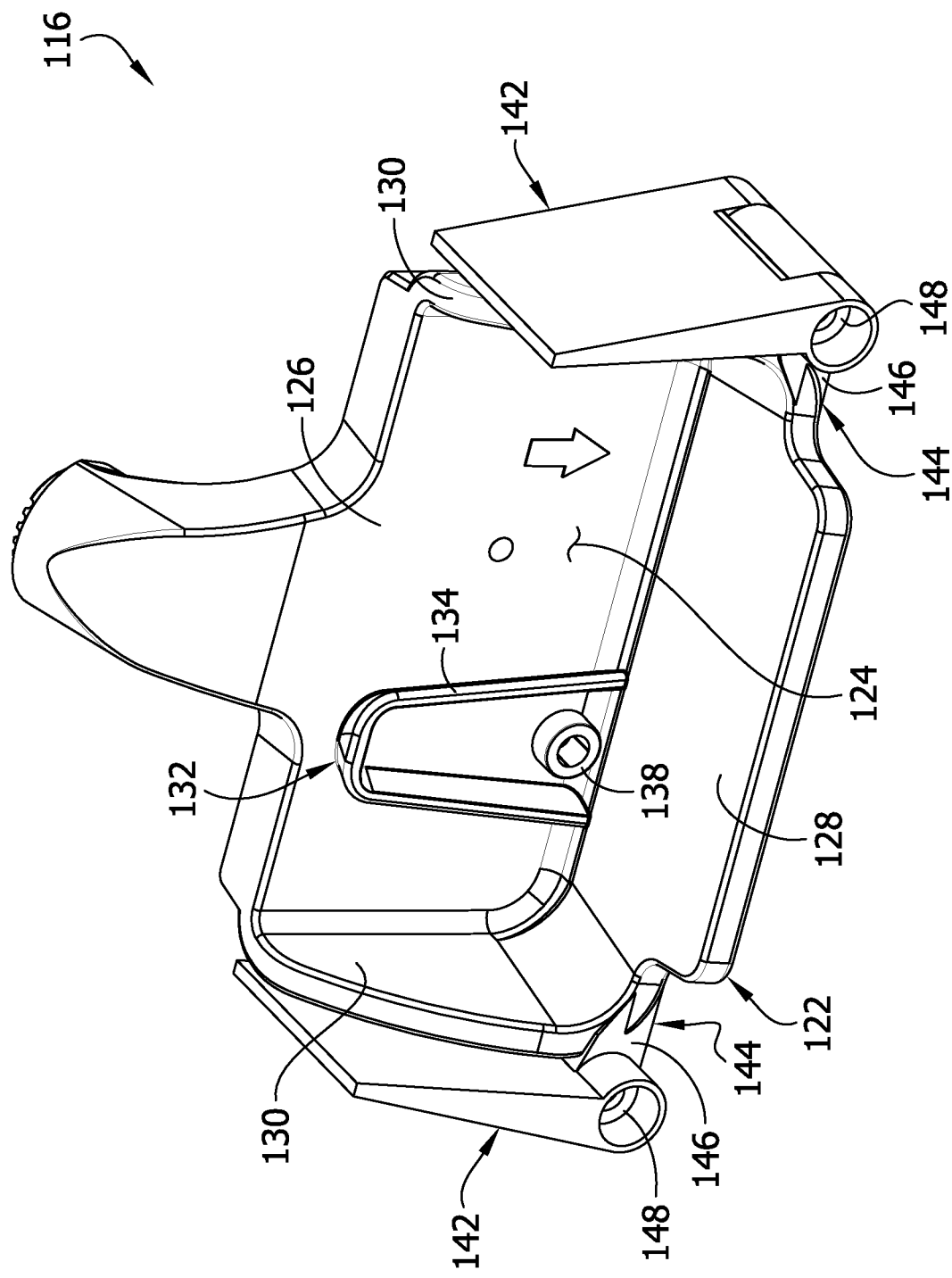
FIG. 22 is a front perspective of another embodiment of a pump support.
Figure 23:
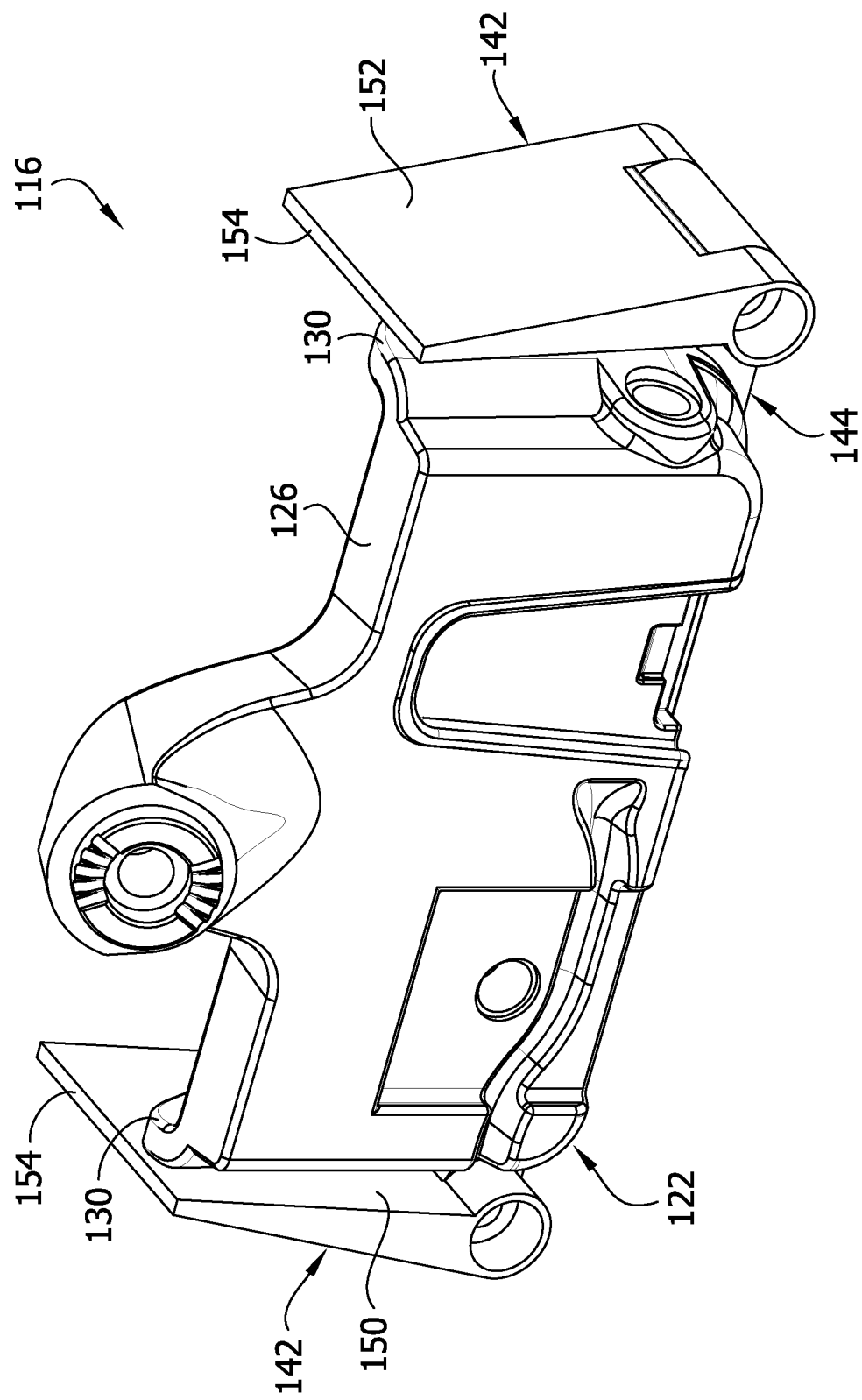
FIG. 23 is a rear perspective of the pump support of FIG. 22.
Figure 24:
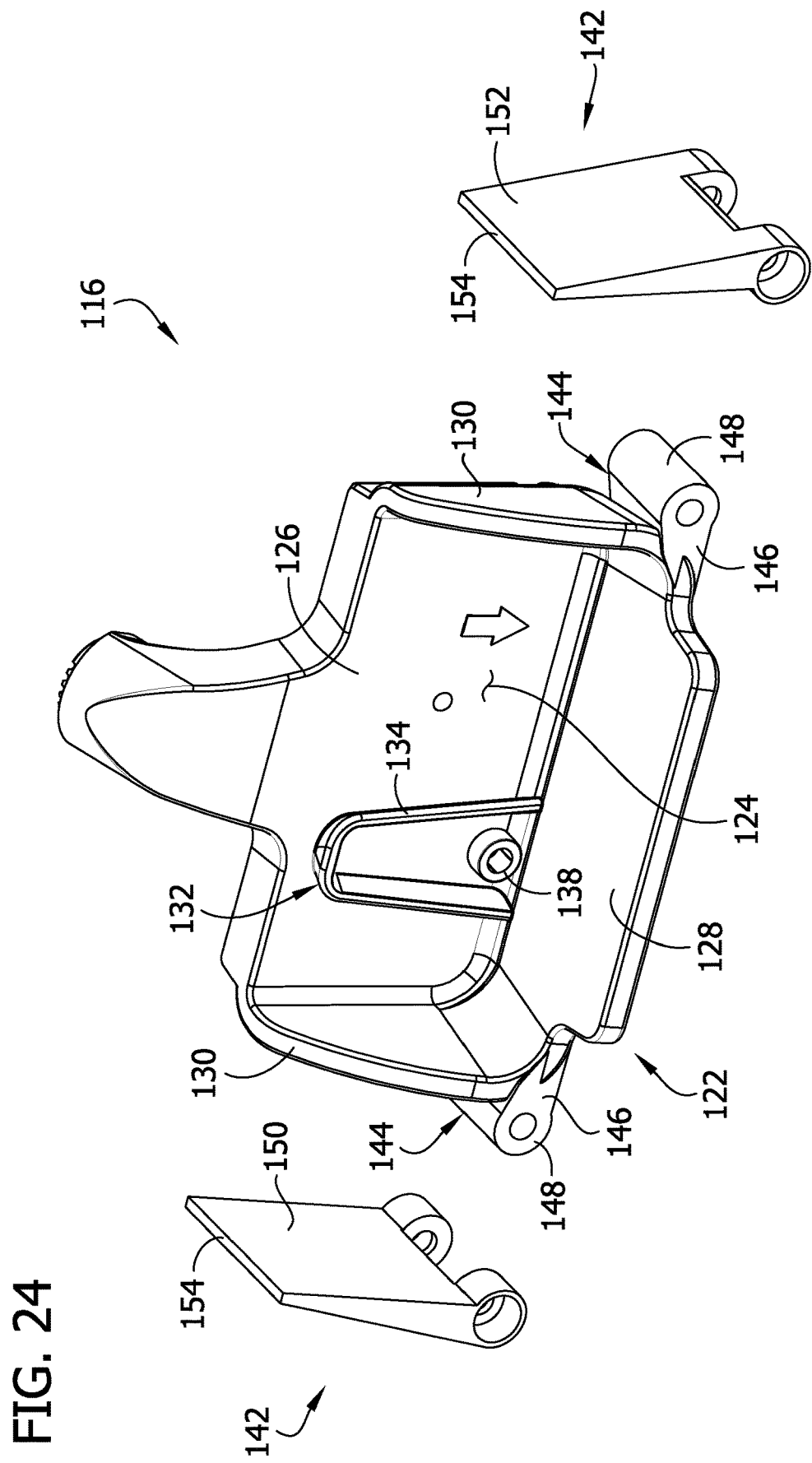
FIG. 24 is an exploded view of the pump support of FIG. 22.

Referring to FIGS. 20 and 21, it has been found that orienting the tip 24 of the syringe upward when delivering breast milk to an infant provides a significant increase in the delivery of fat within the initial stages of delivery. In a comparison study, center-tip syringes filled with breast milk were oriented at different angular positions during feeding cycles and the amount and time of fat delivery was monitored throughout the delivery process. In particular, the study monitored breast milk deliver in syringes held at a horizontal angular orientation, at a 25 degree angle to horizontal with the syringe tip facing upward, at a 45 degree angle to horizontal with the syringe tip facing upward, at a vertical orientation where the syringe is positioned at a 90 degree angle to horizontal with the syringe tip facing upward, and a vertical orientation where the syringe is positioned at a 90 degree angle to horizontal with the syringe tip facing downward. Generally speaking, the syringes that were oriented such that the tips of the syringes were facing upward delivered a larger percentage of the fat portion of the breast milk earlier in the delivery cycle. Conversely, the syringes oriented with their tips facing downward delivered the lowest percentage of the fat portion of the breast milk in the earlier stages of the delivery cycle.

The feeding cycle for each syringe orientation lasted for 60 minutes. Of the five syringe orientations, the vertical orientation with the syringe tip facing upward was the most effective at delivering the fat content of the breast milk within the early stages of the feeding cycle. Referring to FIG. 21, within the first 20 minutes of the feeding cycle, over 40% of the total amount of fat in the breast milk was delivered. In one embodiment, over 44% of the total amount of fat was delivered within the first 20 minutes. Moreover, within a portion of that time, each quantity of breast milk being delivered included over 10% fat (FIG. 20). In one embodiment, for at least 5 minutes within the first 20 minutes of delivery each quantity of breast milk being delivered included over 10% fat. None of the other orientations were able to reproduce these fat delivering capabilities within the first 20 minutes of the delivery cycle.

Referring to FIG. 21, within the first 30 minutes of the feeding cycle, over 60% of the total amount of fat in the breast milk was delivered. In one embodiment, over 63% of the total amount of fat was delivered within the first 30 minutes. Moreover, within a portion of that time, each quantity of breast milk being delivered included over 10% fat (FIG. 20). In one embodiment, for at least 10 minutes within the first 30 minutes of delivery each quantity of breast milk being delivered included over 10% fat. None of the other orientations were able to reproduce these fat delivering capabilities within the first 30 minutes of the delivery cycle.

Referring to FIG. 21, within the first 40 minutes of the feeding cycle, over 65% of the total amount of fat in the breast milk was delivered. In one embodiment, over 70% of the total amount of fat was delivered within the first 40 minutes. In one embodiment, over 71% of the total amount of fat was delivered within the first 40 minutes. Within the first 50 minutes of the feeding cycle, over 80% of the total amount of fat in the breast milk was delivered. In one embodiment, over 84% of the total amount of fat was delivered within the first 50 minutes. Finally, by the completion of the feeding cycle, over 90% of the total amount of fat was delivered. In one embodiment, over 94% of the total amount of fat was delivered by the end of the feeding cycle.

With the syringe 14 loaded in the holder 62 of the pump support 16 and attached to the tubing 77, the pump 1 is configured for delivering the feeding solution in the syringe to a subject. Operation of the pump 1 causes the rollers 43 to engage the tube 45 in the cassette shell 9 to pump the feeding solution from the syringe 14 to the subject. Engagement of the tube 45 by a roller 43 causes the rollers 43 to occlude the tube 45. If the pump support 16 is configured such that the syringe is oriented in the vertical orientation with the tip 24 facing upward, gravity does not assist in drawing feeding fluid out of the syringe. Additionally, there is no direct actuation of the plunger 20 that forces fluid upward out of the barrel 18. Thus, as the rotor 37 rotates to occlude the tube 45 with the rollers 34, air, not liquid, is first drawn out of the inlet tubing 77 and barrel 18 of the syringe 14 which increases the vacuum pressure within the syringe. After a sufficient number of rotor rotations, a vacuum is created in the inlet tubing 77 and syringe 14. Continued rotation of the rotor 37 will draw feeding fluid from the barrel 18 into the inlet tubing 77 through the inlet port 69 and tubing 45 of the cassette shell 9 to be pumped by the pump 1 into the outlet tubing 83 to the subject. However, rotation of the rotor 37 does not produce a continuous uniform flow of feeding fluid through the feeding set 7 as may be the case in traditional pumping arrangements where the outlet of the syringe is oriented such that gravity aids in expelling the feeding fluid downward out of the syringe. To the contrary, fluid is drawn from the syringe 14 in segments or increments which are irregular in volume and discontinuous in time. For example, during a first period of rotor rotation no fluid is drawn from the syringe 14. In this period, the plunger 20 remains stationary with respect to the barrel 18. Eventually, rotation of the rotor 37 causing the vacuum in the fluid line will draw a first volume of fluid from the syringe 14 to be pumped to the subject. The plunger 20 lurches farther into the barrel 18 as the first incremental volume is delivered, but then stops again as vacuum pressure drops. The operation of the pump motor to drive rotation of the rotor may be temporarily stopped after a movement of the plunger 20 of a sufficient amount (for example, and without limitation, movement associated with at least about 0.1 ml of liquid being delivered). Once the movement is detected, there is a delay before the stopped position of the plunger is read, to allow the motion to stop. Temporarily stopping the rotation of the rotor 37 halts the increase of vacuum pressure in the feeding line to help prevent the formation of air bubbles. Rotation is restarted after rotor rotation has been stopped for a period of time, as will be described more fully hereinafter. Continued rotation of the rotor 37, however, will not cause a constant flow of fluid out of syringe 14. Rather, a second period of time will elapse while the rotor 37 is being rotated where no fluid is drawn from the syringe 14. Eventually, this further rotation of the rotor 37 will cause the plunger 20 to lurch forward again into the barrel 18 and a second incremental volume of fluid to be drawn from the syringe 14. This process continues for the entire feeding cycle. The volume of fluid drawn from the syringe 14 in each segment may vary as well as the periods of time between the fluid draws. Thus, in order to deliver the prescribed amount of nutrient liquid to the subject, a feed time calculation is made which takes into consideration the nonlinear fluid delivery produced by the pump 1.

The pump 1 can be programmed or otherwise controlled for operation in a desired manner. For instance, the pump 1 can begin operation to provide feeding fluid from the syringe 14 to the subject. A user such as a caregiver may select (for example) the amount of fluid to be delivered, the flow rate of the fluid, and the frequency of fluid delivery. The pump 1 may have a controller 72 (FIG. 19) including a processor such as a microprocessor 89 that allows it to accept programming and/or to include pre-programmed operational routines, e.g., algorithm, that can be initiated by the user. The controller 72 may also be connected to the pump motor 27 for controlling its operation to actuate the rotor 37.

The amount of feeding fluid that is delivered to the subject is typically controlled by the number of rotations of the rotor 37 (in a counterclockwise direction as viewed in FIG. 3). In the exemplarily illustrated embodiment, the rotor 37 includes three rollers 43 so that each one-third of a rotation delivers one aliquot of fluid to the subject. As each roller 43 first engages the tubing 45, it pinches off the tubing thereby closing off an amount of fluid forward (i.e., toward the subject) from the fluid coming from the feeding source. The roller 43 continues in the counterclockwise rotation which pushes the pinched-off volume of fluid forward of the roller, e.g., the aliquot, toward the subject. Finally, the leading roller 43 releases engagement with the tubing 45 at about the same time the trailing roller engages the tubing for pinching it off for delivering the next aliquot of fluid. Thus, when the microprocessor 89 receives a command to deliver a selected fluid flow rate, it would typically calculate the number of rotations within a given period of time that will deliver a number of aliquots producing the desired flow rate. The selected flow rate may be a rate that is input or selected by the doctor, nurse or other caregiver, or may be a default feeding rate pre-programmed into the pump 1.

However, as described above, the pump 1 does not produce a constant flow of fluid when the rotor 37 is operated and the syringe 14 is oriented in a vertical orientation with the tip 24 facing upward. Rather, nutrient liquid is drawn from the syringe 14 in multiple segments or increments which are nearly always non-uniform in volume and time. Accordingly, the controller 72 may comprise a timer 91 and a memory area 93 including a feed time compensator 85 which adjusts the feeding time if the segments of fluid being drawn from the syringe deviate from the programmed flow rate after a period of time has elapsed during the feeding cycle. In the illustrated embodiment, the feed time compensator 85 may include feed time compensation instructions 95 and feed time compensation functions 97. The feed time compensation instructions 95 are machine readable instructions on any suitable medium, broadly identified as the memory area 93. These instructions can be executed by the microprocessor 89. The timer 91 may be initiated in a suitable manner when a feeding cycle (broadly, "operation cycle") is initiated or performed for delivering feeding fluid from the syringe 14 to the subject. The feed time compensator 85 may use this information along with additional parameters of the feeding cycle to compensate for the potentially non-uniform volume of feeding fluid that is delivered during the feeding cycle.

The feed time compensator 85 can operate to adjust the duration of time for delivering the feeding fluid through the feeding set 7 to account for the deviation in feeding fluid volume drawn for the syringe 14 and delivered to the subject during the time the pump 1 operates in the feeding phase. This adjustment factor may be dependent on a selected or preprogrammed flow rate for the feeding fluid, a volume of feeding fluid delivered to the subject, and the amount of time the pump 1 has been operating in the feeding cycle. More specifically, the controller 72 may employ the following function to determine an adjusted or compensated feed time:

$$X = (Y + Y_1)/(Z + Z_n)$$

X is the selected flow rate for the feeding fluid during the feeding cycle. Y is a volume of the feeding fluid drawn from the syringe 14 and considered in all previous compensation calculations in the feeding cycle. $Y_1$ is a volume of feeding fluid drawn from the syringe 14 since the previous compensation calculation. Z is the total time elapsed since the onset of the feeding cycle to the beginning of the feed compensation operation. $Z_n$ is an adjusted or compensated feeding cycle time that is added to the total feeding cycle time. The function can be stored in the controller 72 so that when one or more of the factors are input into the pump 1 by the caregiver (or included in a preprogrammed feed setting), the microprocessor 79 can calculate the feeding time adjustment $Z_n$ according to the equation $Z_n=(Y+Y_1-XZ)/X$. The feed time compensator 85 provides computer-executable instructions 86 for use in calculating $Z_n=(Y+Y_1-XZ)/X$. In one embodiment, the feed time calculation is performed after each segment or increment of fluid is drawn from the syringe 14 while rotation of the rotor 37 is stopped. The feed compensation functions 97 will then cause the pump 1 to pause in operation by an amount of time $Z_n$ to bring the actual fluid flow rate close to the selected fluid flow rate.

In practice, there may be several very small movements of the plunger 20 with respect to the barrel 18 before a significant volume of fluid is delivered in a larger movement. In one embodiment, these smaller movements are ignored. In other words, the feed time compensator 85 may not initiate the feed time compensation calculation until a threshold volume of feeding fluid has been drawn from the syringe 14. For instance, the feed time compensation calculation may not be run until movement associated with at least about 0.05 mL of fluid has been detected. The threshold for onset of the feed time compensation calculation may be other than described, for example and without limitation the threshold may be 1 ml, 2 ml or more within the scope of the present invention.

Further, by using the "lurch" fluid delivery approach, a system is produced in which only the minimum amount of vacuum needed to move the syringe is created. By using the smallest vacuum possible, the formation of air bubbles in the liquid is greatly reduced and in some cases eliminated. Having air bubbles suspended in the liquid creates gross measurement accuracy errors and is therefore undesirable.

Additionally or alternatively, the feed time compensator 85 may compare the $Y+Y_1$ value (volume of the feeding fluid previously drawn from the syringe 14 plus the most current increment) to the desired total volume of feeding fluid to be delivered to the subject. If Y is within a predetermined range of the desired total volume then the feeding cycle will be stopped. For instance, if Y is within 0.1 mL of the desired total volume then the feeding cycle will be stopped. Other ranges (e.g., 0.05 ml, 0.15 ml, 0.2 ml, 0.25 ml, 0.3 ml, etc.) may be used without departing from the scope of the disclosure.

In embodiments where a camera is used to detect the position of the plunger 20 of the syringe 14 relative to the stand 16 and barrel 18, the camera may pick any reference point on the plunger and determine the length of movement by monitoring the changing position of the selected reference point. As stated previously herein, the camera may also be used to detect the type (e.g., brand or size) of syringe so that the appropriate cross sectional area (or diameter) of the internal volume is known to calibrate the linear movement with the delivered fluid volume. However, in cases where the internal diameter of a particular syringe barrel is not known, calibration of the controller 72 can be undertaken by a comparison of the linear movement of the plunger 20 with respect to the barrel 18 and stand 16 with the actual volume of fluid delivered. For example, in a calibration mode of the pump 1, a syringe 14 filled with a liquid may be installed on the stand 16 and connected to the pump. The pump 1 can be initiated to cause liquid to be delivered from the syringe 14. The user is asked to enter the amount and the controller 72 keeps track of the position of the plunger 20 in the barrel 18 for the measured amount. This operation is repeated according to instructions appearing on the pump display to generate several data points of plunger position and volume delivered. These points can be used in a line fitting calculation to calibrate the controller 72 for operation with the particular syringe. The information can be saved in the controller 72 so that it can be used whenever a syringe 14 of the particular type calibrated is used.

Alternatively, the controller 72 of the pump 1 can be programmed to instruct a user to perform a series of syringe operations to advance the plunger 20 in the barrel 18 and the microprocessor 89 can record the movement of the syringe to calibrate the movement with the volume of liquid dispensed. For example, the controller 72 could instruct the user to move the plunger 20 in the barrel 18 of the syringe 14 to the 0 mL mark and then verify that the action was taken. The microprocessor 89 would then record the measurement. This process can be repeated again at the center of the syringe where instructions can be given to move the syringe to another volume marker (e.g. 30 mL). The microprocessor 89 will then record the distance the syringe (i.e., barrel 18) moved. Finally, instructions can be provided to move the plunger 20 in the syringe 14 to another volume marker, such as at or near the end of the barrel 18. The microprocessor 89 will again record the distance the syringe moved. Using these three data points, a straight line curve calibration for the syringe can be produced.

Thus it may be seen that the various objects and features are achieved by the various embodiments disclosed herein. The pump controller 72 has the feed time compensator 85 that allows the microprocessor 89 to adjust the duration of time for operating the rotor 37 to deliver the feeding fluid through the feeding set 7 to account for the deviation in volume drawn for the syringe 14 and delivered to the subject during the time the pump 1 operates in the feeding phase. Therefore, the subject can receive more accurate volume amounts of feeding fluid for a given feeding cycle.

Referring to FIGS. 22-25, a pump support of another embodiment is generally indicated at 116. The pump support 116 is configured to receive the pump 1 and support the pump on a horizontal support surface S such as a tabletop. The holder 116 comprises a base 122 defining a pocket 124 for receiving the pump 1 therein. The base 122 includes a rear wall 126, a bottom wall 128 projecting forwardly from the rear wall, and a pair of side walls 130 projecting upwardly from the bottom wall and forwardly from the rear wall at opposite sides of the rear wall. A mount 132 may be disposed on the rear wall 126. In the illustrated embodiment, the mount 132 has a rounded triangular or arched shape and includes a mounting flange 134 that diverges on opposite sides of the mount generally from a top of the base toward the bottom wall 128. The mounting flange 134 of the mount 132 may be configured to slidingly engage the groove 136 (FIG. 4A) formed in a back surface of the pump 1 to mount the pump to the support 116. A post 138 may be disposed on the rear wall 126 within the perimeter of the mount 132 and may have a receptacle for receiving a retainer (not shown) for locking the pump 1 to the base 122.

Legs 142 are pivotably attached to respective attachment arms 144 disposed at a bottom of the base 122. Each attachment arm 144 extends from a respective opposite side of the base 122 generally between the bottom wall 128 and a respective side wall 130. Each attachment arm 144 includes an extension portion 146 and a pivot portion 148 at an end of the extension portion. The legs 142 pivot about the pivot portion 148 of the attachment arm 144. Each leg 142 includes a planar top surface 150, a planar bottom surface 152, and an edge surface 154 connecting the top and bottom surfaces. The legs 142 may pivot upward until they engage a corresponding side wall 130, and downward until they engage the extension portion 146 of the attachment arm 144 to which they are attached. In one embodiment, each leg 142 is configured to pivot over a range of about 180 degrees. However, other pivot ranges are envisioned.

Figure 25:
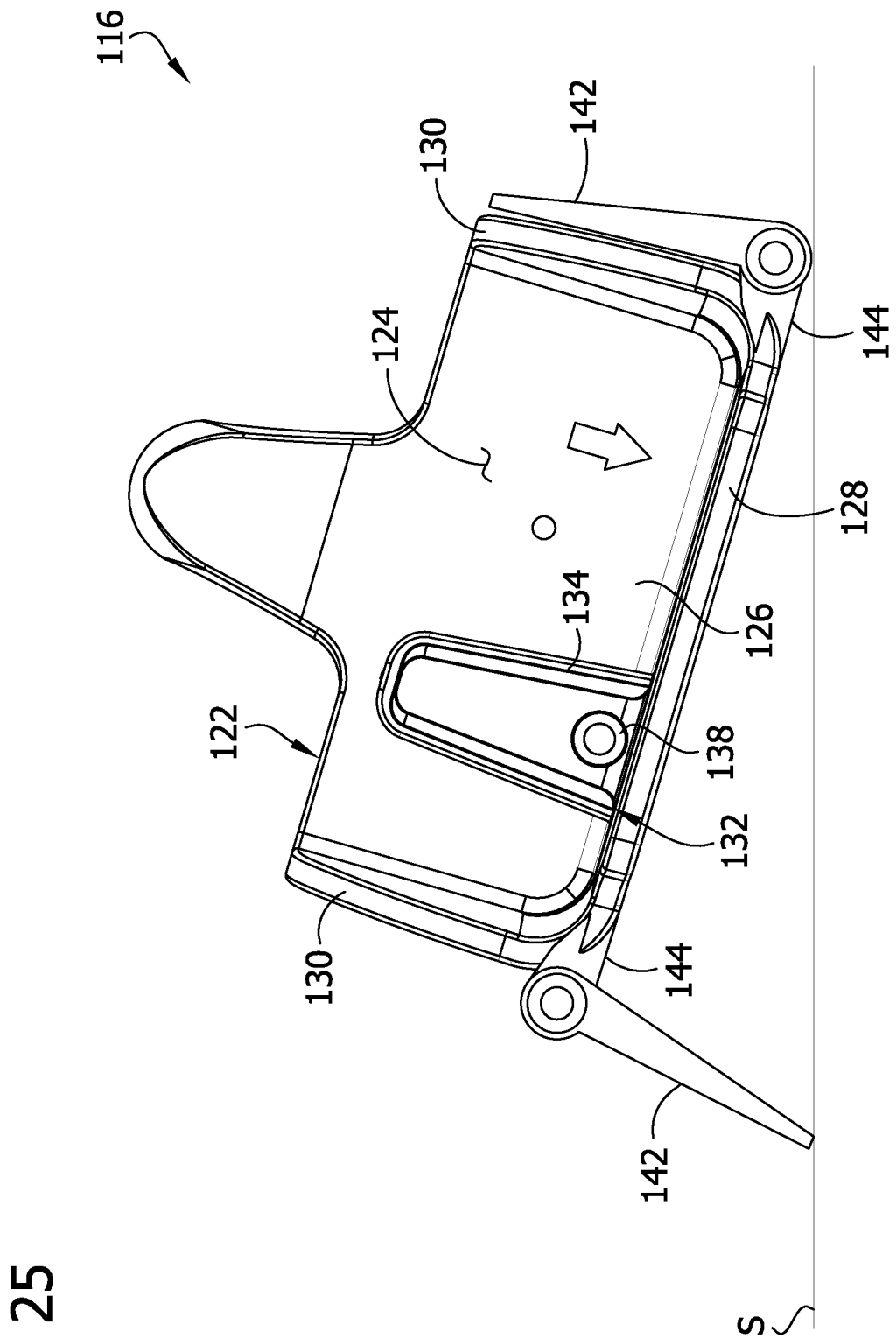
FIG. 25 is a front view of the pump support with a leg of the pump support pivoted to engage a support surface to orient the pump support in an angled orientation.

When the support 116 is supported on a horizontal support surface S, each leg 142 is independently pivotable and configured to pivot about an axis defined by the pivot portion 148. As such, the legs 142 are configured to pivot toward the support surface for engagement with the support surface, and away from the support surface to disengage at least a portion of the legs from the support surface. For example, one of the legs 142 may be pivoted to engage the bottom surface 152 and/or edge surface 154 of the leg with the support surface S (e.g., as shown in FIG. 25) to lift or tilt one side of the support 116, and pump 1 on the support, above the other side to change the angular orientation of the pump. For a pump 1 with a syringe mounted thereon in a horizontal orientation this can cause the tip of the syringe to tilt upward or downward depending on the direction in which the tip faces and the leg that is pivoted to engage the support surface. In the instance where the tip of the syringe is tilted upward, this will provide a similar function to the pump support 16 where the syringe will be oriented at an angle to the horizontal and vertical axes. As discussed above, this orientation has benefits when breast milk is being delivered from the syringe. The legs 142 are configured to angle the support 116 at an angle between about 1 and about 40 degrees with respect to a horizontal axis when the holder is seated on a horizontal support surface. The legs 142 may also be operated to orient a syringe mounted on the pump 1 in other orientations without departing from the scope of the disclosure. The pump support 116 is also configured for attachment to a clamp device (not shown) for attaching the pump support to a support such as an IV pole.

Embodiments may be described in the general context of computer-executable instructions, such as program modules, executed by one or more computers or other devices. The computer-executable instructions may be organized into one or more computer-executable components or modules including, but not limited to, routines, programs, objects, components, and data structures that perform particular tasks or implement particular abstract data types. Aspects may be implemented with any number and organization of such components or modules. For example, various features or aspects are not limited to the specific computer-executable instructions or the specific components or modules illustrated in the figures and described herein. Other embodiments may include different computer-executable instructions or components having more or less functionality than illustrated and described herein.

Further, the order of execution or performance of the operations in any of the embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of one or more aspects.

In operation, microprocessor 89 of the controller 72 executes computer-executable instructions such as those illustrated in the figures to implement one or more aspects disclosed herein. Any of the various aspects may also be practiced in distributed computing environments where tasks are performed by remote processing devices that are linked through a communications network. In a distributed computing environment, program modules may be located in both local and remote computer storage media including memory storage devices.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

Other Aspects of the Disclosure

A1. A pump set for use with a flow control apparatus having a pumping system including a rotor for rotation about a pump axis and at least one roller mounted on the rotor for engaging the pump set, the pump set comprising:
  tubing configured for engagement by the pumping system of the flow control apparatus to pump feeding fluid through the tubing; and
  a syringe assembly connected to the tubing, the syringe assembly comprising a syringe and a stand configured to support the syringe in a generally vertical orientation, the syringe as supported by the stand being oriented such that an outlet of the syringe in fluid communication with the tubing faces generally upward when the syringe is supported on the stand.

A2. The pump set as set forth in A1, wherein the stand is configured to hold the plunger in a fixed position relative to the stand.

A3. The pump set as set forth in A2, wherein the stand comprises a base and a guide wall projecting upwardly from the base, the base being formed to capture an end of the plunger.

A4. The pump set as set forth in A3, wherein the stand further comprises a gripper mounted for movement along the guide wall, the gripper being configured to hold the barrel of the syringe about the base of the stand.

A5. The pump set as set forth in A2 or A3 wherein the base is constructed to rest on a supporting surface with the guide wall extending upwardly from the supporting surface and the syringe extending upwardly from the base.

B1. A syringe assembly for use with a flow control apparatus, the syringe assembly comprising:
  a syringe for holding a volume of feeding fluid, the syringe comprising a barrel for holding the volume of feeding fluid and a plunger movable in the barrel to draw fluid into and force fluid out of the barrel;
  a stand comprising a support configured to support the syringe in a feeding position; and
  a position sensor attached to the stand and configured to detect movement of the syringe barrel with respect to the stand that is indicative of the feeding fluid being delivered out of the barrel.

B2. A syringe assembly as set forth in B1, wherein the position sensor comprises one of a potentiometer, a camera, a magnetic foil sensor, and a non-magnetic induction sensor.

B3. A syringe assembly as set forth in B1 or B2 wherein the stand comprises a gripper configured to connect to the barrel of the syringe, the gripper being movable with respect to the stand.

B4. A syringe assembly as set forth in B3, wherein the gripper is connected to the position sensor.

B5. A syringe assembly as set forth in B1, wherein the position sensor comprises a camera, the syringe assembly further comprising a controller configured to detect the type of syringe installed on the stand.

C1. A flow control apparatus for use with a pump set to deliver fluid from a feeding source through the pump set to a subject, the flow control apparatus comprising:
  a pumping device capable of acting on the pump set to produce a fluid flow within the pump set during a feeding cycle; and
  a controller in communication with the pumping device for controlling operation of the pumping device in a feeding configuration for producing flow of a fluid in the pump set, the controller including a processor and a memory, the controller being adapted to store in the memory a selected flow rate and a desired fluid volume of the fluid, the controller configured to execute in the processor a feed time compensator to adjust a feed time for operating the pumping device for delivering the fluid through the pump set during the feeding cycle to account for a detected deviation in actual flow rate from the feeding source from the selected flow rate.

C2. The flow control apparatus as set forth in C1, wherein the controller pauses operation of the pumping device to compensate for the detected deviation of the actual flow rate from the selected flow rate.

C3. The flow control apparatus as set forth in C1 or C2 wherein the controller compares a total actual delivered volume of fluid with the desired volume of the fluid and ends the feeding cycle if the difference is within a predetermined threshold.

C4. The flow control apparatus as set forth in any one of C1-C3 wherein the feed time compensator calculates the compensated feed time based on the equation: $X=(Y+Y_1)/(Z+Z_n)$ where X is the selected flow rate for the fluid, Y is a volume of the fluid already delivered from the feeding source during the feeding cycle, $Y_1$ is a volume of feeding fluid delivered from the feeding source since the most recent prior compensation calculation, Z is a total time elapsed in the feeding cycle, and $Z_n$ is a feed time adjustment.

C5. The flow control apparatus as set forth in any one of C1-C4, wherein the controller is programmed to execute the feed time compensator only after a threshold volume of fluid has been delivered from the feeding source.

D1. A method of delivering fluid from a syringe having a barrel and a plunger received in the barrel using a pumping device of a flow control apparatus that acts on a pump set attached to the flow control apparatus to produce fluid flow through the pump set, the method comprising:
  inputting into a controller of the pumping device at least one of a selected flow rate and a total volume of fluid to be delivered from the syringe during a cycle of operation;
  initiating operation of the pumping device using the controller to draw fluid from the syringe;
  detecting relative movement between the plunger and the syringe and sending a signal representative of the detected relative movement to the controller;
  calculating using computer executable instructions in the controller a compensated feed time for operating the pumping device to deliver the fluid through the pump set during the cycle of operation to compensate for any deviation in the rate at which fluid is actually delivered from the syringe and the selected flow rate; and
  operating the flow control apparatus to deliver the fluid through the pump set at the compensated feed time.

D2. The method as set forth in D1, wherein the controller delays onset of operation of the pumping device by the calculated compensated feed time.

D3. The method as set forth in D1 or D2 wherein the controller halts operation of the pumping device upon detection of relative movement between the plunger and the syringe.

D4. The method as set forth in D3, wherein the controller halts operation of the pumping device upon detection of relative movement between the plunger and the syringe that exceeds a predetermined threshold movement.

D5. The method as set forth in any one of D1-D4, wherein the compensated feed time is calculated when the pumping device is not operating to pump fluid through the pump set.

E1. A method of delivering breast milk to an infant, the method comprising:
  retrieving breast milk stored in a syringe having a barrel and a plunger received in the barrel;
  attaching the syringe to a stand so that a longitudinal axis of the syringe is generally vertical with an outlet of the syringe being located at a top; and
  delivering breast milk from the syringe while in the stand to the infant.

E2. The method as set forth in E1, wherein delivering the breast milk comprises drawing breast milk from the syringe by applying a vacuum pressure to the outlet of the syringe.

E3. The method as set forth in A1 or E2 wherein delivering the breast milk includes moving the barrel of the syringe with respect to the stand and plunger.

F1. A method of calibrating a flow control apparatus used to deliver fluid from a syringe to a subject, the method comprising:
  causing an instruction to appear on a display of the flow control apparatus to initiate a calibration routine stored by the flow control apparatus;
  saving an initial position of a plunger of the syringe relative to a barrel of the syringe;
  delivering a first amount of the fluid from the syringe;
  prompting entry into the flow control apparatus of the first amount of fluid delivered;
  saving a second position of the plunger;
  operating the flow control apparatus to deliver a second amount of fluid;
  prompting entry into the flow control apparatus of the second amount of fluid delivered;
  saving a third position of the plunger;
  determining within the flow control apparatus a displacement/amount relationship between displacement of the plunger relative to the barrel of the syringe and amount of fluid delivered;
  storing the displacement/amount relationship in a memory of the flow control apparatus; and
  storing a syringe identifier for the syringe whereby the flow control apparatus is able to recall the displacement/amount relationship for use of the syringe in a later delivery of fluid.

G1. A method of calibrating a flow control apparatus used to deliver fluid from a syringe to a subject, the method comprising:

causing an instruction to appear on a display of the flow control apparatus to initiate a calibration routine stored by the flow control apparatus;
saving in the flow control apparatus an initial position of a plunger of the syringe relative to a barrel of the syringe;
causing an instruction to appear to move the plunger relative to the barrel to a second position at a first known volume marker;
recording in the flow control apparatus movement of the plunger relative to the barrel from the initial position to the second position;
causing an instruction to appear to move the plunger relative to the barrel to a third position at a second known volume marker;
recording in the flow control apparatus movement of the plunger relative to the barrel from the second position to the third position;
determining within the flow control apparatus a displacement/volume relationship between displacement of the plunger relative to the barrel of the syringe and volume of fluid delivered; and
storing the displacement/volume relationship in a memory of the flow control apparatus.

G2. The method of G1 further comprising storing a syringe identifier for the syringe whereby the flow control apparatus is able to recall the displacement/volume relationship for use of the syringe in a later delivery of fluid.

H1. A method of delivering fluid from a syringe having a barrel and a plunger received in the barrel using a pumping device of a flow control apparatus that acts on a pump set attached to the flow control apparatus to produce fluid flow through the pump set, the method comprising:
inputting into a controller of the pumping device at least one of a selected flow rate and a total volume of fluid to be delivered from the syringe during a cycle of operation;
initiating operation of the pumping device using the controller to draw fluid from the syringe;
detecting relative movement between the plunger and the syringe and sending a signal representative of the detected relative movement to the controller;
halting operation of the pumping device to limit the vacuum pressure in the syringe; and
re-starting the pumping device.

I1. A flow control apparatus for use with a pump set to deliver fluid from a feeding source through the pump set to a subject, the flow control apparatus comprising:
a pumping device capable of acting on the pump set to produce a fluid flow within the pump set during a feeding cycle; and
a controller in communication with the pumping device for controlling operation of the pumping device in a feeding configuration for producing flow of a fluid in the pump set, the controller including a processor and a memory, the controller being adapted to store in the memory a selected flow rate and a desired fluid volume of the fluid, the controller configured to operate the pumping device to limit vacuum pressure delivered on the feeding source.

J1. A flow control apparatus for use with a pump set to deliver fluid from a feeding source through the pump set to a subject, the flow control apparatus comprising:
a pumping device capable of acting on the pump set to produce a fluid flow within the pump set during a feeding cycle; and
a controller in communication with the pumping device for controlling operation of the pumping device in a feeding configuration for producing flow of a fluid in the pump set, the controller, the controller being configured upon detection of delivery of a predetermined amount of feeding solution from the feeding source to stop the operation of the pumping device.

J2. The flow control apparatus as set forth in J1 wherein the feeding source is a syringe including a barrel and a plunger received in the barrel, wherein the controller stops the pumping device when a predetermined movement of the plunger is detected.

K1. An enteral feeding system for delivering fluid to a subject comprising:
a feeding set assembly including a cassette and tubing mounted to the cassette;
a syringe assembly including a syringe connected to the tubing and a stand configured to support the syringe, the stand including a base for supporting the stand on a horizontal support surface, and a holder for securing the syringe to the stand, the holder being attachable to the base and selectively positionable relative to the base to orient the syringe in at least two different positions; and
a flow control apparatus including a pumping device capable of acting on the tubing to draw fluid from the syringe to produce a fluid flow within the feeding set.

L1. A feeding set assembly for use with a flow control apparatus comprising:
a cassette configured for releasable attachment to the flow control apparatus, the cassette including an inlet port;
tubing connected to the inlet port; and
a valve assembly connected to the tubing, the valve assembly including a valve housing and a valve actuatable between a closed position preventing ambient air from entering the tubing and an open position permitting ambient air to enter the tubing to purge the tubing of fluid in the tubing.

M1. A method of delivering fortifier from a syringe to a subject using a pumping device of a flow control apparatus, the method comprising:
providing the syringe with a volume of fortifier including a total amount of preferred nutrient and an amount of non-preferred nutrient liquid;
mounting the syringe relative to the flow control apparatus;
orienting the syringe in a generally vertical orientation such that an outlet of the syringe faces downward;
initiating operation of the pumping device to draw the fortifier from the syringe; and
delivering at least a portion of the volume of fortifier from the syringe to the subject such that the preferred nutrient in the fortifier is preferentially delivered from the syringe.

What is claimed:
1. A syringe stand for supporting a syringe including a barrel having an outlet and a plunger received in an end of the barrel opposite the outlet, the syringe stand comprising:
a base for supporting the syringe stand on a horizontal support surface; and
a holder for securing the syringe to the syringe stand, the holder being attachable to the base and selectively positionable relative to the base to orient the syringe in at least two different positions, wherein the holder comprises a receptacle configured to receive at least a portion of the barrel and plunger of the syringe; and a guide assembly configured to guide movement of the plunger in the receptacle, the guide assembly comprising at least one rail and a slide moveable along the rail, wherein movement of the plunger moves the slide along the rail to guide the movement of the plunger in the receptacle.

2. The syringe stand of claim 1, wherein the holder is positionable in a first position where the syringe is oriented in a generally vertical orientation such that a longitudinal axis of the syringe is generally parallel to a vertical axis and the outlet of the syringe faces upward, and a second position where the syringe is oriented generally horizontal such that the longitudinal axis of the syringe is generally parallel to a horizontal axis.

3. The syringe stand of claim 2, wherein the holder is positionable in a third position where the longitudinal axis of the syringe is oriented at an angle with respect to the vertical and horizontal axes.

4. The syringe stand of claim 1, wherein the holder is configured to hold the barrel of the syringe in a fixed position relative to the stand.

5. The syringe stand of claim 1, further comprising a position sensor attached to the holder and configured to detect movement of the plunger with respect to the holder indicative of fluid being delivered out of the barrel.

6. The syringe stand of claim 5, wherein the position sensor comprises one of a potentiometer, a camera, a magnetic foil sensor, and a non-magnetic induction sensor.

7. The syringe stand of claim 1, wherein the base is configured to mount a flow control apparatus to the base.

8. The syringe stand of claim 7, further comprising a pass-thru connector on the base, the connector including a port and a plug in communication with the port, the plug being configured to connect with a port on the flow control apparatus, and the port on the base being configured to receive the plug to connect the plug with the port on the flow control apparatus though the connector.

9. The syringe stand of claim 1, wherein the base includes a mount for attaching to a clamp to mount the syringe stand to a vertical support.

10. The syringe stand of claim 1, wherein the at least one rail includes a first rail and a second rail.

11. The syringe stand of claim 5, wherein the position sensor is configured to detect movement of the plunger based on movement of the slide along the at least one rail.

* * * * *